(12) United States Patent
Rydzak et al.

(10) Patent No.: US 10,179,907 B2
(45) Date of Patent: Jan. 15, 2019

(54) GENE MODIFICATION IN CLOSTRIDIUM FOR INCREASED ALCOHOL PRODUCTION

(71) Applicant: UT-Battelle, LLC, Oak Ridge, TN (US)

(72) Inventors: Thomas Rydzak, Calgary (CA); Adam M. Guss, Knoxville, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

(21) Appl. No.: 15/643,580

(22) Filed: Jul. 7, 2017

(65) Prior Publication Data

US 2018/0057807 A1 Mar. 1, 2018

Related U.S. Application Data

(60) Provisional application No. 62/359,248, filed on Jul. 7, 2016.

(51) Int. Cl.
| | |
|---|---|
| *C12P 7/16* | (2006.01) |
| *C12N 9/00* | (2006.01) |
| *C12P 7/06* | (2006.01) |
| *C12P 7/10* | (2006.01) |

(52) U.S. Cl.
CPC ............... *C12N 9/93* (2013.01); *C12P 7/065* (2013.01); *C12P 7/10* (2013.01); *C12P 7/16* (2013.01); *C12Y 603/01002* (2013.01)

(58) Field of Classification Search
CPC ...................................................... C12P 7/16
USPC .............................. 435/160, 161, 188, 252.3
See application file for complete search history.

(56) References Cited

PUBLICATIONS

Argyros, D.A. et al., "High Ethanol Titers from Cellulose by Using Metabolically Engineered Thermophilic, Anaerobic Microbes", Applied and Environmental Microbiology, Dec. 2011, vol. 77, No. 23, p. 8288-8294.
Biwas, R. et al., "Elimination of hydrogenase active site assembly blocks H2 production and increases ethanol yield in Clostridium thermocellum", Biswas et al. Biotechnology for Biofuels (2015) 8:20, pp. 1-8.
Desvaux, M. et al., "Carbon Flux Distribution and Kinetics of Cellulose Fermentation in Steady-State Continuous Cultures of Clostridium cellulolyticum on a Chemically Defined Medium", Journal of Bacteriology, Jan. 2001, vol. 183, No. 1, p. 119-130.
Desvaux, M. et al., "Kinetics and Metabolism of Cellulose Degradation at High Substrate Concentrations in Steady-State Continuous Cultures of Clostridium cellulolyticum on a Chemically Defined Medium", Applied and Environmental Microbiology, Sep. 2001, vol. 67, No. 9, p. 3837-3845.
Desvaux, M. et al., "Metabolic flux in cellulose batch and cellulosefed continuous cultures of Clostridium cellulolyticum in response to acidic environment", Microbiology (2001), 147, 1461-1471.
Guedon, E. et al., "Carbon and Electron Flow in Clostridium cellulolyticum Grown in Chemostat Culture on Synthetic Medium", Journal of Bacteriology, May 1999, vol. 181, No. 10, p. 3262-3269.
Guss, A. M. et al., "Dcm methylation is detrimental to plasmid transformation in Clostridium thermocellum", Guss et al. Biotechnology for Biofuels 2012, 5:30, p. 1-6.
Holwerda, E.K. et al., "The exometabolome of Clostridium thermocellum reveals overflow metabolism at high cellulose loading", Holwerda et al. Biotechnology for Biofuels 2014, 7:155, p. 1-11.
Rydzak, T. et al., "Proteomic analysis of Clostridium thermocellum core metabolism: relative protein expression profiles and growth phase-dependent changes in protein expression", Rydzak et al. BMC Microbiology 2012, 12:214, p. 1-18.
Rydzak, T. et al., "Insights into electron flux through manipulation of fermentation conditions and assessment of protein expression profiles in Clostridium thermocellum", Appl Microbiol Biotechnol (2014) 98:6497-6510, p. 1.
Rydzak, T. et al., "Elimination of formate production in Clostridium thermocellum", J Ind Microbiol Biotechnol (2015) 42:1263-1272.
Tripathi, S. A. et al., "Development of pyrF-Based Genetic System for Targeted Gene Deletion in Clostridium thermocellum and Creation of a pta Mutant", Applied and Environmental Microbiology, Oct. 2010, vol. 76, No. 19, p. 6591-6599.
Van Der Veen, D. et al., "Characterization of Clostridium thermocellum strains with disrupted fermentation end-product pathways", J Ind Microbiol Biotechnol (2013) 40:725-734.
Wang, S. et al., "NADP+ Reduction with Reduced Ferredoxin and NADP+ Reduction with NADH Are Coupled via an Electron-Bifurcating Enzyme Complex in Clostridium kluyveri", Journal of Bacteriology, Oct. 2010, vol. 192, No. 19, p. 5115-5123.
Wilson, C.M. et al., "Clostridium thermocellum transcriptomic profiles after exposure to furfural or heat stress", Biotechnology for Biofuels 2013, 6:131, p. 1-13.
Papanek, B. et al., "Elimination of metabolic pathways to all traditional fermentation products increases ethanol yield in Clostriudium thermocellum", Metabolic Engineering, (2015), vol. 32, pp. 49-54.
Ellis, L.D. et al., "Closing the carbon balance for fermentation by Clostriudium themocellum (ATCC 27405)", Bioresource Technology, (2012), 103, pp. 293-299.
Deng, Y. et al., "Redirecting carbon flux through exogenous pyruvate kinase to achieve high ethanol yields in Clostridium thermocellum", Metabolic Engineering, (2013), 15, pp. 151-158.

*Primary Examiner* — Tekchand Saidha
(74) *Attorney, Agent, or Firm* — Scully Scott Murphy & Presser

(57) ABSTRACT

The present disclosure is directed to genetically engineered bacteria strains with enhanced biofuel-producing capabilities from cellulosic substrates. The bacteria strains of the present disclosure comprise an inactivated Type I glutamine synthetase gene. The present disclosure is also directed to methods of producing biofuels from cellulosic biomass using the genetically engineered bacteria strains.

18 Claims, 6 Drawing Sheets
(2 of 6 Drawing Sheet(s) Filed in Color)
Specification includes a Sequence Listing.

SEQUENCE LISTING

<160> NUMBER OF SEQ ID NOS: 20

<210> SEQ ID NO 1

```
<211> LENGTH: 62
<212> TYPE: DNA
<213> ORGANISM: Artificial Sequence
<220> FEATURE:
<223> OTHER INFORMATION: Oligonucleotide

<400> SEQUENCE: 1
attttgtttc ccataggcgc gccgatattt taaatactc aatcaaaaca cattttgctc      60
tg                                                                    62

<210> SEQ ID NO 2
<211> LENGTH: 64
<212> TYPE: DNA
<213> ORGANISM: Artificial Sequence
<220> FEATURE:
<223> OTHER INFORMATION: Oligonucleotide

<400> SEQUENCE: 2
cacgcataat tagccgagaa tatggccagc ggccgctaag attttctaag ataagtcggt      60
ggtt                                                                  64

<210> SEQ ID NO 3
<211> LENGTH: 26
<212> TYPE: DNA
<213> ORGANISM: Artificial Sequence
<220> FEATURE:
<223> OTHER INFORMATION: Oligonucleotide

<400> SEQUENCE: 3
tggccatatt ctcggctaat tatgcg                                          26

<210> SEQ ID NO 4
<211> LENGTH: 67
<212> TYPE: DNA
<213> ORGANISM: Artificial Sequence
<220> FEATURE:
<223> OTHER INFORMATION: Oligonucleotide

<400> SEQUENCE: 4
ttcaatagtt tagataaaaa ataattaatt ttttaaacgg aacaatttat attcacggaa      60
acagtgg                                                               67

<210> SEQ ID NO 5
<211> LENGTH: 36
<212> TYPE: DNA
<213> ORGANISM: Artificial Sequence
<220> FEATURE:
<223> OTHER INFORMATION: Oligonucleotide

<400> SEQUENCE: 5
ttaaaaaatt aattattttt tatctaaact attgaa                               36

<210> SEQ ID NO 6
<211> LENGTH: 28
<212> TYPE: DNA
<213> ORGANISM: Artificial Sequence
<220> FEATURE:
<223> OTHER INFORMATION: Oligonucleotide

<400> SEQUENCE: 6
atgaatacat ttcaggtttc aaaacgcc                                        28

<210> SEQ ID NO 7
<211> LENGTH: 56
```

```
<212> TYPE: DNA
<213> ORGANISM: Artificial Sequence
<220> FEATURE:
<223> OTHER INFORMATION: Oligonucleotide

<400> SEQUENCE: 7
ggcgttttga aacctgaaat gtattcataa tcccctttgt caagggcgc catatc        56

<210> SEQ ID NO 8
<211> LENGTH: 63
<212> TYPE: DNA
<213> ORGANISM: Artificial Sequence
<220> FEATURE:
<223> OTHER INFORMATION: Oligonucleotide

<400> SEQUENCE: 8
tatacactcc gctagcgcgg atccgatagg atgagttata atataaaaat aaaagaggtg   60
ctg                                                                 63

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide

<400> SEQUENCE: 9
ccctctaggc gcataggaac                                               20

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide

<400> SEQUENCE: 10
ccataacgat ttcgttgtaa gaag                                          24

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
atgaataccc gttctgtatc                                               20

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide

<400> SEQUENCE: 12
caatagcgac ggagagttag g                                             21

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide
```

<400> SEQUENCE: 13
ttgattacag aagaagagtt gaagg                                    25

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide

<400> SEQUENCE: 14
tcataatccc ctttgtcaag g                                        21

<210> SEQ ID NO 15
<211> LENGTH: 27
<212> TYPE: DNA
<213> ORGANISM: Artificial Sequence
<220> FEATURE:
<223> OTHER INFORMATION: Oligonucleotide

<400> SEQUENCE: 15
tttaagaata tttcttgaat ctccctc                                  27

<210> SEQ ID NO 16
<211> LENGTH: 27
<212> TYPE: DNA
<213> ORGANISM: Artificial Sequence
<220> FEATURE:
<223> OTHER INFORMATION: Oligonucleotide

<400> SEQUENCE: 16
tataaaaata aaagaggtgc tggagtt                                  27

<210> SEQ ID NO 17
<211> LENGTH: 27
<212> TYPE: DNA
<213> ORGANISM: Artificial Sequence
<220> FEATURE:
<223> OTHER INFORMATION: Oligonucleotide

<400> SEQUENCE: 17
gcctaaaatg tttcttacaa aactact                                  27

<210> SEQ ID NO 18
<211> LENGTH: 30
<212> TYPE: DNA
<213> ORGANISM: Artificial Sequence
<220> FEATURE:
<223> OTHER INFORMATION: Oligonucleotide

<400> SEQUENCE: 18
gacttcatat taatatatct ctttcaaagg                               30

<210> SEQ ID NO 19
<211> LENGTH: 28
<212> TYPE: DNA
<213> ORGANISM: Artificial Sequence
<220> FEATURE:
<223> OTHER INFORMATION: Oligonucleotide

<400> SEQUENCE: 19
ttgaccattt ttcaatttat tattcatc                                 28

<210> SEQ ID NO 20
<211> LENGTH: 27

```
<212> TYPE: DNA
<213> ORGANISM: Artificial Sequence
<220> FEATURE:
<223> OTHER INFORMATION: Oligonucleotide

<400> SEQUENCE: 20
aaaattgtct gggacaaaga tatattg                                           27
```

GENE MODIFICATION IN CLOSTRIDIUM FOR INCREASED ALCOHOL PRODUCTION

CROSS REFERENCE TO RELATED APPLICATION

This application claims the benefit of priority from U.S. Provisional Application No. 62/359,248, filed Jul. 7, 2016, the entire contents of which are incorporated herein by reference.

STATEMENT REGARDING FEDERALLY SPONSORED RESEARCH OR DEVELOPMENT

This invention was made with government support under Prime Contract No. DE-AC05-000R22725 awarded by the U.S. Department of Energy. The government has certain rights in the invention.

INCORPORATION BY REFERENCE OF SEQUENCE LISTING

The Sequence Listing in an ASCII text file, named as 35129_3625_Seq_ST25.txt of 5 KB, created on Jul. 5, 2017, and submitted to the United States Patent and Trademark Office via EFS-Web, is incorporated herein by reference.

BACKGROUND

Increasing global energy demands, depletion of low extraction-cost fossil fuel reserves, and environmental concerns are driving forces for the search for renewable and environmentally friendly energy sources. Bioethanol is among the leading alternatives to petroleum-derived fossil fuels for the transportation sector given that it is compatible with current engine technologies, burns cleaner than gasoline, has a high octane/cetane number, and can be derived from renewable biomass feedstocks (Arora et al., 2015. *Renew Sust Energ Rev.* 51, 699-717; Vohra et al., 2014. *J. of Env. Chem. Eng.* 2, 573-584). The USA and Brazil are among the leaders in ethanol production, generating 14.8 and 7.1 billions of gallons of ethanol in 2015, respectively. Of the total global bioethanol produced, roughly 50% is derived from maize and 30% is derived from sugarcane. This dependence of bioethanol production on food/feed crops may increase food costs and increases the volatility of ethanol prices (Vohra et al., 2014. *J. of Env. Chem. Eng.* 2, 573-584). Life cycle analysis has further shown that substituting gasoline with cellulosic ethanol can reduced greenhouse gas emission by up to 115%, versus a 19-48% reduction with corn ethanol (Wang et al., 2012. *Environ Res Lett.* 7). Thus, a transition to lignocellulosic feedstocks for bioethanol production is needed.

Currently, bioethanol is predominantly made via fermentation of mono- or disaccharides using *Saccharomyces cerevisiae* or *Zymomonas mobilis*. While these organisms are capable of high ethanol yields and titers, they cannot natively deconstruct highly recalcitrant lignocellulosic biomass to liberate fermentable sugars (Himmel et al., 2007. *Abstr Pap Am Chem S.* 233). Thus, lignocellulosic bioethanol production using these organisms requires chemical and/or enzymatic hydrolysis of lignocellulosic biomass, separate cellulase production, and subsequent fermentation, increasing production costs. Alternatively, a number of organisms are capable of cellulase-mediated cellulose hydrolysis and subsequent fermentation to ethanol via consolidated bioprocessing (CBP), potentially allowing for enhanced process economics (Lynd et al., 2005. *Curr. Op. in Biotech.* 16, 577-83; Lynd et al., 2002. *Microbio. and Mol. Bio. Rev.* 66, 506-77). However, to date, none can produce ethanol at yields and titers sufficient for economic viability.

*Clostridium thermocellum* is a promising candidate for lignocellulosic bioethanol production via CBP because it has the innate ability to rapidly solubilize raw biomass with minimal or no pre-treatment (Paye et al., 2016. *Biotech. for Biofuels.* 9), and ferment resulting cellulosic hydrolysis products into ethanol. However, due to branched product pathways that divert carbon and electrons to products other than ethanol, wild type *C. thermocellum* ethanol yields are approximately 30% of the theoretical maximum of 2 moles ethanol per mole hexose, well below industrial requirement of approximately 90%. The remaining carbon is used to produce canonical fermentation products (acetate, lactate, formate, and $H_2$) as well as secreted amino acids (primarily valine and alanine) (Ellis et al., 2012. *Bioresource Technol.* 103, 293-9; Kridelbaugh et al., 2013. *Bioresource Technol.* 130, 125-135; van der Veen et al., 2013. *J Ind Microbiol Biot.* 40, 725-34) and other compounds including pyruvate, malate, fumarate, isobutanol, and butanediol (Holwerda et al., 2014. *J Ind Microbiol Biot.* 39, 943-947), further limiting ethanol yields. Elucidation of metabolic pathways via enzymology (Carere et al., 2014. *Appl Microbiol Biotechnol.* 98, 2829-40; Lamed and Zeikus, 1980. *J BacterioL* 144, 569-78; Lin et al., 1998; Özkan, 2004. *Can. J. of Microbiol.* 50, 845-851; Rydzak et al., 2009. *Journal of Biotechnology.* 140, 169-75; Sparling et al., 2006. *Can J Microbiol.* 52, 681-8; Taillefer et al., 2015. *Appl Environ Microb.* 81, 2423-2432; Zhou et al., 2013), transcriptomics (Carere et al., 2014. *Appl Microbiol Biotechnol.* 98, 2829-40; Deng et al., 2013. *Metab Eng.* 15, 151-8; Raman et al., 2011. *BMC Microbiol.* 11, 134; Wilson et al., 2013. *Biotechnology for Biofuels.* 6, 131; Yang et al., 2012. *BMC Genomics.* 13, 336), proteomics (Raman et al., 2009. *PloS One.* 4, e5271; Rydzak et al., 2014. *Microbiol Biotechnol.* 98, 6497-510; Rydzak et al., 2012. *BMC Microbiology.* 12, 214), and genetics (Argyros et al., 2011. *Appl Environ Microb.* 77, 8288-8294; Biswas et al., 2014. *PloS one.* 9, e86389; Biswas et al., 2015. *Biotechnology for Biofuels.; Deng et al., 2013. Metab Eng.* 15, 151-8; Tripathi et al., 2010. *Appl Environ Microb.* 76, 6591-9), in conjunction with improvements in *C. thermocellum* electrotransformation protocols (Olson and Lynd, 2012. *Methods in Enzymology.* 510, 317-30; Tyurin et al., 2004. *Appl Environ Microbiol.* 70, 883-90), transformation efficiencies (Guss et al., 2012. *Biotechnology for biofuels.* 5, 30), and gene deletion screening methods (Argyros et al., 2011. *Appl Environ Microb.* 77, 8288-8294; Tripathi et al., 2010. *Appl Environ Microb.* 76, 6591-9), has allowed for rational metabolic engineering of *C. thermocellum* to improve ethanol yields by eliminating pathways that lead to canonical fermentation products. While deletion of phosphotransacetylase (pta) (Tripathi et al., 2010. *Appl Environ Microb.* 76, 6591-9) and pyruvate:formate lyase (pfl) (Rydzak et al., 2015. *J Ind Microbiol Biot.* 42, 1263-1272) eliminated acetate and formate production, respectively, marginal impacts on ethanol production were observed. Alternatively, elimination of lactate, lactate and acetate, or $H_2$ via deletion of lactate dehydrogenase (ldh) (Biswas et al., 2014. *PloS One.* 9, e86389), ldh and pta (Argyros et al., 2011. *Appl Environ Microb.* 77, 8288-8294; van der Veen et al., 2013. *J Ind Microbiol Biot.* 40, 725-34), or [FeFe] hydrogenase maturation factor (hydG) and [NiFe] Ech-type hydrogenase (ech) (Biswas et al., 2015. *Biotechnology for Biofuels*), respectively, improved ethanol production. While deletion of all but one of these genes (ech) in a single strain (ΔhydG Δpfl Δpta-ack Δldh; strain AG553) resulted in the highest ethanol yielding *C. thermocellum* strain to date (Papanek et al., 2015. *Metab Eng.* 32, 49-54), ethanol yields typically ranged from 50-70% of the theoretical maximum, which is still below the benchmark 90% ethanol yields achieved by *Saccharomyces cerevisiae* or *Zymomonas mobilis*. Recently strain AG553 was evolved to grow faster, resulting in a strain able to produce 25 g/L ethanol at 75% of the theoretical maximum yield (Tian et al., 2016. *Biotechnology for Biofuels.* 9).

Recent studies have demonstrated that secreted amino acids typically account for approximately 4-10% of total substrate consumed in wild type *C. thermocellum*, reaching as high as 17% in certain mutants (i.e. evolved Δldh Δpta strain), with valine and alanine accounting for the bulk of these amino acids (Ellis et al., 2012. *Bioresource Technol.* 103, 293-9; Holwerda et al., 2014. *J Ind Microbiol Biot.* 39, 943-947; Kridelbaugh et al., 2013. *Bioresource Technol.* 130, 125-135; van der Veen et al., 2013. *J Ind Microbiol Biot.* 40, 725-34). The extent of amino acid secretion has also been shown to be dependent on medium nitrogen content (Kridelbaugh et al., 2013. *Bioresource Technol.* 130, 125-135) and carbon loading (Holwerda et al., 2014, *J Ind Microbiol Biot.* 39, 943-947), and has been proposed to alleviate carbon and electron imbalances. While few studies have measured amino acid secretion in other cellulolytic organisms, free amino acids in *Clostridium cellulolyticum* fermentations medium have been reported to account for 15% and 6% of total carbon consumed on cellobiose and cellulose, respectively (Desvaux et al., 2001. *Journal of Bacteriology.* 183, 119-130; Desvaux et al., 2001. *Appl Environ Microb.* 67, 3837-3845; Desvaux et al., 2001. *Microbiol-Sgm.* 147, 1461-1471; Guedon et al., 1999, *Journal of Bacteriology.* 181, 3262-3269), demonstrating that amino acid secretion in cellulolytic bacteria is not exclusive to *C. thermocellum*. In *C. cellulolyticum*, 30-fold higher protein/DNA ratios in supernatants versus cell extracts suggest that cell lysis is not the cause of amino acids in the medium (Guedon et al., 1999. *Journal of Bacteriology.* 181, 3262-3269).

In most bacteria, ammonium assimilation typically occurs via glutamate dehydrogenase (GLDH) or through the combination of glutamine synthetase (GS) and glutamine-oxoglutarate aminotransferase/glutamate synthase (GOGAT). GLDH catalyzes the reductive amination of α-ketoglutarate to glutamate using NAD(P)H, typically under nitrogen-rich conditions (Shimizu, 2013. *ISRN Biochem,* 645983). Alternatively, under nitrogen-limited conditions, ATP-dependent GS aminates glutamate to glutamine, and NAD(P)H or ferredoxin-dependent GOGAT replenishes the glutamate pool using glutamine and α-ketoglutarate. GSs can be divided into four groups, including Type I GSs (~450 aa in length) which are widely distributed among bacteria and archeabacteria, Type II GSs (~360 aa) which are typically found in plants and some soil bacteria, Type III GSs (~730 aa) which have been identified in anaerobic bacteria and cyanobacteria, and the enigmatic GlnT family of poorly characterized GSs (van Rooyen et al., 2011. *Acta Cryst. Sec. F. Str. Bio. Cryst. Comm.,* 67, 358-363). Type I GSs can be further divided into Type Iα, typically found in the Firmicutes and the Archaea, and Type Iβ found in many other groups (Brown et al., 1994. *J. Mol. Evol.,* 38, 566-576).

With the exception of one by Bogdahn and Kliener (1986. *Arch Microbiol.* 145, 159-161), little has been done to elucidate nitrogen assimilation in *C. thermocellum*. Enzyme activity studies showed high NADPH-dependent glutamate dehydrogenase (GLDH) and moderate glutamine synthetase (GS) activities, but failed to detect any NADH or NADPH-dependent glutamine-oxoglutarate aminotransferase/glutamate synthase (GOGAT) activity (Bogdahn and Kleiner, 1986. *Arch Microbiol.* 145, 159-161). While RNA-seq studies show variable expression of these genes, the Type I gs, gldh, and two of the five genes in a cluster containing putative gogat genes are typically expressed at high levels (Gowen and Fong, 2010. *Biotechnol J.* 5, 759-767; Wilson et al., 2013. *Biotechnology for Biofuels.* 6, 131).

SUMMARY OF THE DISCLOSURE

In one aspect, this disclosure provides genetically engineered bacteria strains with enhanced alcohol production from cellulosic substrates, wherein said bacteria strains comprise an inactivated Type I glutamine synthetase gene (glnA) (e.g. *C. thermocellum* Genbank Acc. No: ADU75074.1).

In some embodiments, the bacteria strains are strains of *Clostridium*. In a specific embodiment, the bacteria strains are strains of *Clostridium thermocellum* (*C. thermocellum*).

In some embodiments, the bacteria strains further comprise at least one inactivated gene selected from the list consisting of spoOA encoding the master regulator of sporulation (e.g., *C. thermocellum* Genbank Acc. No: ADU73717.1), NfnAB complex encoding the ferredoxin-NADH:NADP+ oxidoreductase (described in e.g., Lo et al, 2015. *J Bacteriol. September;* 197(18):2920-9), ppdK encoding pyruvate:phosphate dikinase(e.g., *C. thermocellum* Genbank Acc. No: CDG35979.1), mdh encoding malate dehydrogenase(e.g., *C. thermocellum* Genbank Acc. No: WP_003512586.1), mae encoding malic enzyme (e.g., *C. thermocellum* Genbank Acc. No: CDG35022.1), pta encoding phosphotransacetlylase (e.g., *C. thermocellum* Genbank Acc. No: CDG35723.1), pfl encoding pyruvate:formate lyase (e.g., *C. thermocellum* Genbank Acc. No: ANV76478.1), ldh encoding lactate dehydrogenase (e.g., *C. thermocellum* Genbank Acc. No: ADU74930.1), hydG encoding [FeFe] hydrogenase maturation factor, and ech encoding [NiFe] Ech-type hydrogenase (e.g., *C. thermocellum* Genbank Acc. No: WP_003520976.1).

In some embodiments, the bacteria strains further comprise at least one overexpressed gene selected from the list consisting of Rnf encoding Ferredoxin:NADH oxidoreductase (e.g., *C. thermocellum* Genbank Acc. Nos: ABN53636.1 and ABN53637.1), PDC encoding pyruvate decarboxylase (e.g., *C. ventriculi* Genbank Acc. No: AAL18557.1), adhE encoding bifunctional aldehyde/alcohol dehydrogenase (e.g., *C. thermocellum* Genbank Acc. No: AKK25366.1), and pryK encoding pyruvate kinase (e.g., *C. pasteurianum* Genbank Acc. No: KRU11172.1). In some embodiments, overexpression of genes is achieved by heterologous expression from an exogenously introduced vector.

In some embodiments, the inactivation of the Type I glutamine synthetase (glnA) gene in cells is achieved by deleting or mutating the Type I glutamine synthetase (glnA) gene in whole or in part such that no functional Type I glutamine synthetase (glnA) protein product is expressed.

In some embodiments, the inactivation of the Type I glutamine synthetase (glnA) gene in bacteria is achieved by a method selected from the group consisting of CRISPR/Cas system, Cre/Lox system, TALEN system and homologous recombination.

In a further aspect, the present disclosure provides methods of producing biofuels from cellulosic biomass based on use of the bacterial strains described herein.

In another aspect, this disclosure provides improved methods of producing alcohol from a cellulosic substrate comprising adding genetically modified bacteria to a fermentation mixture, wherein the genetic modification is inactivation of a Type I glutamine synthetase (glnA) gene in said bacteria, allowing said bacteria to ferment and produce alcohol, and recovering the alcohol produced.

In some embodiments, the produced alcohol is ethanol, butanol, or isobutanol, or a combination thereof. In a specific embodiment, the fermentation is carried out anaerobically at a temperature of about 50-65 °C. In specific embodiments, the efficiency of alcohol production is at least 70%, at least 75%, at least 80%, at least 85%, at least 90%, at least 95% or at least 99% of the theoretical maximum, wherein theoretical maximum refers to the production of 2 moles of alcohol per one mole of hexose.

In yet another aspect, the present disclosure provides methods of producing a genetically engineered bacteria strain with enhanced alcohol production from cellulosic substrates comprising inactivating in a bacteria strain the endogenous gene coding for Type I glutamine synthetase (glnA), or introducing into a bacteria strain an exogenous nucleic acid encoding a protein comprising a mutant Type I glutamine synthetase (glnA) gene.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Definitions

Figure 1:
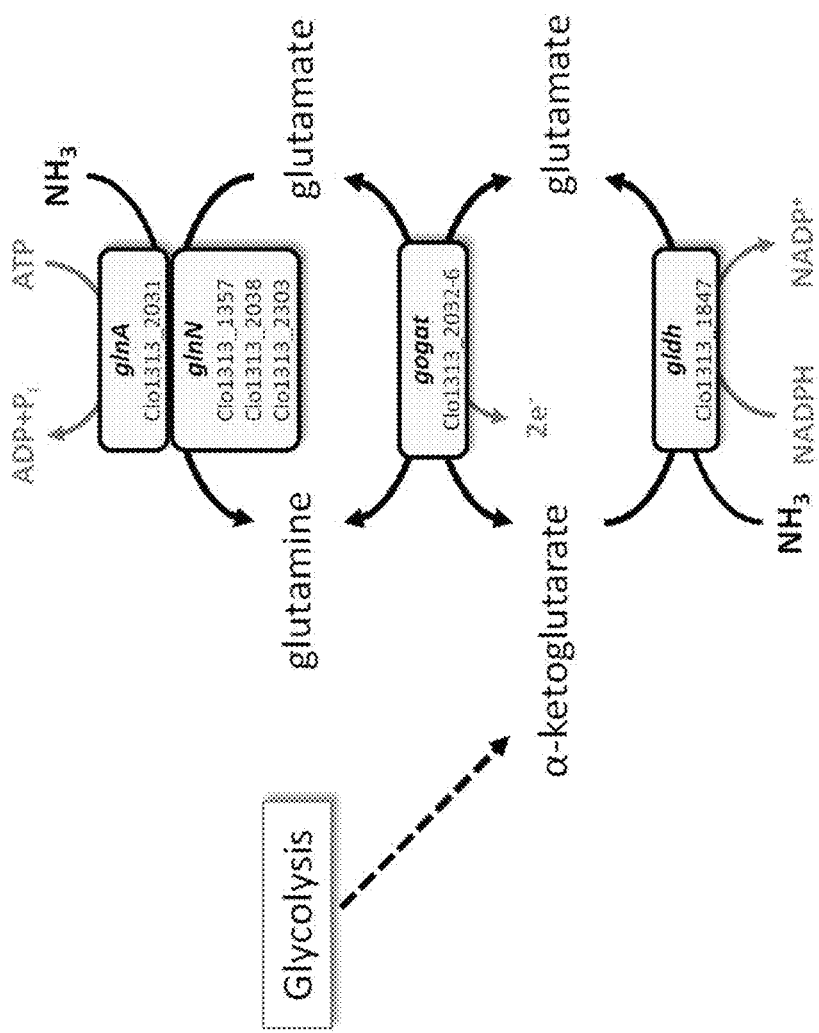
FIG. 1: Nitrogen assimilation pathway in *C. thermocellum* based on genome annotation. glnA, Type I glutamine synthetase; glnN, Type III glutamine synthetase; gogat, glutamine-oxoglutarate aminotransferase/glutamate synthase type enzymes; gldh, glutamate dehydrogenase.

Unless defined otherwise, all technical and scientific terms used herein have the same meaning as commonly understood by one of ordinary skill in the art to which this invention belongs.

As used herein, the term "about" refers to an approximately +/−10% variation from a given value.

The term "amination" refers to the process by which an amine group is introduced into an organic molecule.

The term "biomass" refers biological material from living, or recently living organisms, such as wood, waste, (hydrogen) gas, and alcohol fuels. Biomass is carbon, hydrogen and oxygen based. Nitrogen and small quantities of other atoms, including alkali, alkaline earth and heavy metals can be found as well. Metals are often found in functional molecules such as the porphyrins which include chlorophyll which contains magnesium. Plants in particular combine water and carbon dioxide to sugar building blocks. The required energy is produced from light via photosynthesis based on chlorophyll. On average, between 0.1 and 1% of the available light is stored as chemical energy in plants. The sugar building blocks are the starting point for all of the major fractions found in terrestrial plants, lignin, hemicellulose and cellulose. Biomass is widely recognized as a promising source of raw material for production of renewable fuels and chemicals.

The term "cellobiose" refers to a disaccharide sugar obtained by the breakdown of cellulose. Cellobiose has the following formula: $[HOCH_2CHO(CHOH)_3]_2O$.

The term "cellulosic biomass" (also "lignocellulose" or "cellulosic substrate") refers to a structural material that comprises much of the mass of plants. Lignocellulose is composed mainly of carbohydrate polymers (cellulose, hemicelluloses) and an aromatic polymer (lignin). As used herein, cellulosic/lignocellulosic biomass includes virgin biomass, waste biomass and energy crops. Virgin biomass includes all naturally occurring terrestrial plants such as trees, bushes and grass. Waste biomass is produced as a low value byproduct of various industrial sectors such as agriculture (corn stover, sugarcane bagasse, straw etc.) and forestry (saw mill and paper mill discards). Energy crops are crops with high yield of lignocellulosic biomass produced to serve as a raw material for production of second generation biofuel; examples include switch grass (*Panicum virgatum*) and Elephant grass.

The term "cellulosic alcohol", as used herein, refers to a biofuel produced from wood, grasses, or the inedible parts of plants. Specifically, cellulosic alcohol is a type of biofuel produced from lignocellulose (aka. cellulosic biomass). In specific embodiments, cellulosic alcohol can be ethanol, butanol, isobutanol, or a combination thereof.

As used herein, the term "CRISPR" refers to a RNA-guided endonuclease comprising a nuclease, such as Cas9, and a guide RNA that directs cleavage of the DNA by hybridizing to a recognition site in the genomic DNA.

The term "DNA," as used herein, refers to a nucleic acid molecule of one or more nucleotides in length, wherein the nucleotide(s) are nucleotides. By "nucleotide" it is meant a naturally-occurring nucleotide, as well modified versions thereof. The term "DNA" includes double-stranded DNA, single-stranded DNA, isolated DNA such as cDNA, as well as modified DNA that differs from naturally-occurring DNA by the addition, deletion, substitution and/or alteration of one or more nucleotides as described herein.

As used herein, the term "fermentation mixture" refers to a mixture comprising untreated or pretreated cellulosic (lignocellulosic) biomass and one or more ethanol fermentive microorganisms. A fermentation mixture may comprise the fiber fraction of a pretreated cellulosic biomass that has been previously subject to partial or complete enzymatic hydrolysis and/or used in a simultaneous saccharification and fermentation process. A fermentation mixture may comprise a starch/cellobiose biomass, a cellulosic biomass or a mixture of both.

Fiber fraction of a pretreated lignocellulosic biomass is obtained from pretreatment and/or post-pretreatment processes in which pretreated biomass is separated into at least two fractions, one comprising predominantly liquid, and one comprising insoluble materials having water content. The fiber fraction is that fraction comprising insoluble materials having water content. The liquid fraction and fiber fraction may be separated in multiple steps. For example, a pre-treated biomass may be pressed once, separating a liquid and fiber fraction, then subsequently washed and pressed again, separating, again, a liquid and fiber fraction. A fiber fraction may be subject to enzymatic or chemical hydrolysis and liquefaction prior to use in a fermentation mixture.

The term "gene," as used herein, refers to a segment of nucleic acid that encodes an individual protein or RNA and can include both exons and introns together with associated regulatory regions such as promoters, operators, terminators, 5' untranslated regions, 3' untranslated regions, and the like.

The term "genetically engineered" (or "genetically modified") refers to a microorganism comprising a manipulated genome or nucleic acids.

The term "glutamine synthetase" refers to an enzyme with ExPASy ENZYME entry: EC 6.3.1.2 that plays an essential role in the metabolism of nitrogen by catalyzing the condensation of glutamate and ammonia to form glutamine:

Glutamate+ATP+NH$_3$→Glutamine+ADP+phosphate

The term "heterologous" as used herein refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

The term "heterologous expression", as used herein, shall refer to the protein expression of a gene, a nucleic acid or a cDNA, which is foreign to the organism in which the expression occurs.

The term "hexose" refers to a monosaccharide with six carbon atoms, having the chemical formula $C_6H_{12}O_6$. Examples of hexose include glucose and fructose.

The term "homolog" means a gene related to a second gene by descent from a common ancestral DNA sequence, therefore, the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95%, 97% or 99%). "Type I glutamine synthetase (ginA) gene homolog" furthermore means that the function is equivalent to the function of the Type I glutamine synthetase (ginA) gene.

The term "lactate dehydrogenase" refers to an enzyme that catalyzes the conversion of lactate to pyruvic acid and back, as it converts NAD+ to NADH and back. A dehydrogenase, as used herein, is an enzyme that transfers a hydride from one molecule to another.

As used herein, the term "nucleic acid" has its general meaning in the art and refers to refers to a coding or non coding nucleic sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and non coding region of a genome (i.e. nuclear or mitochondrial).

"Overexpression" or "overexpressed" is defined herein to be at least 150% of protein activity or amount as compared with an appropriate endogenous control. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or upregulating the endogenous gene, and the like. In a specific embodiment, in order to achieve overexpression in amount of a protein, one or more expression vectors encoding the protein is added to the cell.

The term "phosphotransacetylase" refers to an enzyme with the ExPASy ENZYME entry: EC 2.3.1.8 that converts acetyl-CoA and phosphate to acetyl-phosphate and CoA, and vice versa:

acetyl-CoA+phosphate ⇌ CoA+acetyl phosphate

The term "pyruvate:formate lyase" (a.k.a. "Formate C-acetyltransferase") refers to an enzyme with the ExPASy ENZYME entry: EC 2.3.1.54 that catalyzes the reversible conversion of pyruvate and coenzyme-A into formate and acetyl-CoA:

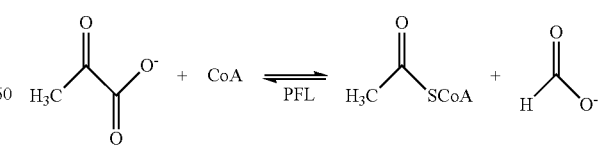

The term "theoretical maximum" in ethanol production refers to the production of 2 moles ethanol per mole hexose. In some embodiments, the efficiency of alcohol production is at least 70% of the theoretical maximum. In specific embodiments, the efficiency is of alcohol production is 70%, 75%, 80%, 85%, 90%, 95%, 99% of the theoretical maximum alcohol production.

General Description

It has been demonstrated herein that inactivation of Type I glutamine synthetase in Clostridium results in enhanced biofuel (e.g. alcohol) production in the fermentation of cellulosic substrates. Accordingly, the present invention is directed to providing genetically engineered bacteria with enhanced efficiency in the fermentation of cellulosic substrates.

Type I Glutamine Synthase (glnA)

As used herein Type I glutamine synthetases are enzymes that are made up of 12 identical subunits, and catalyze the condensation of glutamate and ammonia to form glutamine Examples of Type I glutamine synthetases include *Clostridium thermocellum* gene Genbank Acc. No: ADU75074.1, *Clostridium straminisolvens* gene Genbank Acc. No: GAE87020.1, *Clostridium celatum* gene Genbank Acc. No: WP_005212603.1, *Clostridium disporicum* gene Genbank Acc. No: CU067328.1, *Clostridium leptum* gene Genbank Acc. No: ED062045.1, *Clostridium stercorarium* gene Genbank Acc. No: WP_054632751.1, *Clostridium methylpentosum* gene Genbank Acc. No: WP_006353641.1, *Clostridium bartlettii* gene Genbank Acc. No: CDA11247.1, *Clostridium paraputrificum* gene Genbank Acc. No: WP_055183808.1, *Clostridium josui* gene Genbank Acc. No: WP_024831812.1, *Clostridium clariflavum* gene Genbank Acc. No: AEV70385, *Clostridium papyrosolvens* gene Genbank Acc. No: WP_020815767.1, *Clostridium cellulovorans* gene Genbank Acc. No: YP_003845303.1.

In some embodiments, inactivation of the Type I glutamine synthetase (glnA) in a bacterium results in a substantial inability of said bacterium to aminate glutamate to glutamine By substantial inability, it is meant that the enzymatic activity of the Type I glutamine synthetase (glnA) is reduced by 30%, 40%, 50%, 60%, 70%, 80%, 90%, 95% or nearly 100% of the enzymatic activity. In some embodiments, inactivation of the Type I glutamine synthetase (glnA) a bacterium also results in an enhanced alcohol production of said bacterium during fermentation of cellulosic substrates.

Microorganisms

In some embodiments, the present disclosure provides microorganisms that are genetically engineered to inactivate the Type I glutamine synthetase (glnA) gene. Microorganisms of the present disclosure display enhanced ethanol production from cellulosic substrates as a result of the inactivation of the Type I glutamine synthetase (glnA) gene. Microorganisms encompassed within the scope of the present disclosure include bacterial species.

In some embodiments, the present disclosure provides bacterial strains with enhanced ethanol production from cellulose or cellulosic substrates as a result of inactivation of the Type I glutamine synthetase (glnA) gene or homolog thereof described herein. The Type I glutamine synthetase (glnA) gene may be named differently in different bacterial strains, but comprises an enzyme that catalyzes the condensation of glutamate and ammonia to form glutamine Bacteria that lack a functional Type I glutamine synthase enzyme lack the ability to aminate glutamate to glutamine.

In some embodiments, said bacteria further comprises at least one inactivated gene selected from the list consisting of phosphotransacetlylase (pta), pyruvate:formate lyase (pfl), lactate dehydrogenase (ldh), [FeFe] hydrogenase maturation factor (hydG) and [NiFe] Ech-type hydrogenase (ech).

Bacterial strains of interest include the genus of *Clostridium* including, but not limited to, the following species: *Clostridium absonum, Clostridium aceticum, Clostridium acetireducens, Clostridium acetobutylicum, Clostridium acidisoli, Clostridium aciditolerans, Clostridium acidurici, Clostridium aerotolerans, Clostridium aestuarii, Clostridium akagii, Clostridium aldenense, Clostridium aldrichii, Clostridium algidicarni, Clostridium algidixylanolyticum, Clostridium algifaecis, Clostridium algoriphilum, Clostridium alkalicellulosi, Clostridium aminophilum, Clostridium aminovalericum, Clostridium amygdalinum, Clostridium amylolyticum, Clostridium arbusti, Clostridium arcticum, Clostridium argentinense, Clostridium asparagiforme, Clostridium aurantibutyricum, Clostridium autoethanogenum, Clostridium baratii, Clostridium barkeri, Clostridium bartlettii, Clostridium beijerinckii, Clostridium bifermentans, Clostridium bolteae, Clostridium bornimense, Clostridium botulinum, Clostridium bowmanii, Clostridium bryantii, Clostridium butyricum, Clostridium cadaveris, Clostridium caenicola, Clostridium caminithermale, Clostridium carboxidivorans, Clostridium carnis, Clostridium cavendishii, Clostridium celatum, Clostridium celerecrescens, Clostridium cellobioparum, Clostridium cellulofermentans, Clostridium cellulolyticum, Clostridium cellulosi, Clostridium cellulovorans, Clostridium chartatabidum, Clostridium chauvoei, Clostridium chromiireducens, Clostridium citroniae, Clostridium clariflavum, Clostridium clostridioforme, Clostridium coccoides, Clostridium cochlearium, Clostridium colletant, Clostridium colicanis, Clostridium colinum, Clostridium collagenovorans, Clostridium cylindrosporum, Clostridium difficile, Clostridium diolis, Clostridium disporicum, Clostridium drakei, Clostridium durum, Clostridium estertheticum, Clostridium estertheticum estertheticum, Clostridium estertheticum laramiense, Clostridium fallax, Clostridium felsineum, Clostridium fervidum, Clostridium fimetarium, Clostridium formicaceticum, Clostridium frigidicarnis, Clostridium frigoris, Clostridium ganghwense, Clostridium gasigenes, Clostridium ghonii, Clostridium glycolicum, Clostridium glycyrrhizinilyticum, Clostridium grantii, Clostridium haemolyticum, Clostridium halophilum, Clostridium hastiforme, Clostridium hathewayi, Clostridium herbivorans, Clostridium hiranonis, Clostridium histolyticum, Clostridium homopropionicum, Clostridium huakuii, Clostridium hungatei, Clostridium hydrogeniformans, Clostridium hydroxybenzoicum, Clostridium hylemonae, Clostridium jejuense, Clostridium indolis, Clostridium innocuum, Clostridium intestinale, Clostridium irregulare, Clostridium isatidis, Clostridium josui, Clostridium kluyveri, Clostridium lactatifermentans, Clostridium lacusfryxellense, Clostridium laramiense, Clostridium lavalense, Clostridium lentocellum, Clostridium lentoputrescens, Clostridium leptum, Clostridium limosum, Clostridium litorale, Clostridium lituseburense, Clostridium ljungdahlii, Clostridium lortetii, Clostridium lundense, Clostridium magnum, Clostridium malenominatum, Clostridium mangenotii, Clostridium mayombei, Clostridium methoxybenzovorans, Clostridium methylpentosum, Clostridium neopropionicum, Clostridium nexile, Clostridium nitrophenolicum, Clostridium novyi, Clostridium oceanicum, Clostridium orbiscindens, Clostridium oroticum, Clostridium oxalicum, Clostridium papyrosolvens, Clostridium paradoxum, Clostridium paraperfringens* (Alias: *C. welchii*), *Clostridium paraputrificum, Clostridium pascui, Clostridium pasteurianum, Clostridium peptidivorans, Clostridium perenne, Clostridium perfringens, Clostridium pfennigii, Clostridium phytofermentans, Clostridium piliforme, Clostridium polysaccharolyticum,*

*Clostridium populeti, Clostridium propionicum, Clostridium proteoclasticum, Clostridium proteolyticum, Clostridium psychrophilum, Clostridium puniceum, Clostridium purinilyticum, Clostridium putrefaciens, Clostridium putrificum, Clostridium quercicolum, Clostridium quinii, Clostridium ramosum, Clostridium rectum, Clostridium roseum, Clostridium saccharobutylicum, Clostridium saccharogumia, Clostridium saccharolyticum, Clostridium saccharoperbutylacetonicum, Clostridium sardiniense, Clostridium sartagoforme, Clostridium scatologenes, Clostridium schirmacherense, Clostridium scindens, Clostridium septicum, Clostridium sordellii, Clostridium sphenoides, Clostridium spiroforme, Clostridium sporogenes, Clostridium sporosphaeroides, Clostridium stercorarium, Clostridium stercorarium leptospartum, Clostridium stercorarium stercorarium, Clostridium stercorarium thermolacticum, Clostridium sticklandii, Clostridium straminisolvens, Clostridium subterminale, Clostridium sufflavum, Clostridium sulfidigenes, Clostridium symbiosum, Clostridium tagluense, Clostridium tepidiprofundi, Clostridium termitidis, Clostridium tertium, Clostridium tetani, Clostridium tetanomorphum, Clostridium thermaceticum, Clostridium thermautotrophicum, Clostridium thermoalcaliphilum, Clostridium thermobutyricum, Clostridium thermocellum, Clostridium thermocopriae, Clostridium thermohydrosulfuricum, Clostridium thermolacticum, Clostridium thermopalmarium, Clostridium thermopapyrolyticum, Clostridium thermosaccharolyticum, Clostridium thermosuccinogenes, Clostridium thermosulfurigenes, Clostridium thiosulfatireducens, Clostridium tyrobutyricum, Clostridium uliginosum, Clostridium ultunense, Clostridium villosum, Clostridium vincentii, Clostridium viride, Clostridium xylanolyticum, Clostridium xylanovorans.*

Inactivation of Type I Glutamine Synthetase (glnA)

Inactivation of the Type I glutamine synthetase (glnA) gene in *Clostridium* provides one or more benefits. In one embodiment, inactivation of the Type I glutamine synthetase (glnA) gene in *Clostridium* can increase the production of alcohols during the fermentation of cellulosic substrates. In a specific embodiment, inactivation of the Type I glutamine synthetase (glnA) gene in *Clostridium* can increase the production of ethanol, butanol, or isobutanol, or combinations therof, during the fermentation of cellulosic substrates. In one embodiment, inactivation of the Type I glutamine synthetase (glnA) gene in *Clostridium* can decrease the production of amino acids during the fermentation of cellulosic substrates. In a specific embodiment, inactivation of the Type I glutamine synthetase (glnA) gene in *Clostridium* can decrease the production of valine and alanine amino acids during the fermentation of cellulosic substrates. In one embodiment, inactivation of the Type I glutamine synthetase (glnA) gene in *Clostridium* can decrease the production of lactate and $H_2$ during the fermentation of cellulosic substrates.

Inactivation of the Type I glutamine synthetase (glnA) gene in bacterial cells can be achieved, for example, by genetic inactivation.

Genetic Inactivation of Type I Glutamine Synthetase (glnA)

In some embodiments, the inactivation of the Type I glutamine synthetase (glnA) gene includes a deletion of the whole or a part of the gene such that no functional protein product is expressed (also known as gene knock out). The inactivation of a gene may include a deletion of the promoter or the coding region, in whole or in part, such that no functional protein product is expressed. In other embodiments, the inactivation of Type I glutamine synthetase (glnA) includes introducing an inactivating mutation to the gene, such as an early STOP codon in the coding sequence of the gene, such that no functional protein product is expressed. Deletion or inactivation of the Type I glutamine synthetase (glnA) gene in a microorganism leads to significant enhancement in the production of ethanol from cellulose or cellulosic substrates.

In some embodiments, gene inactivation is achieved using available gene targeting technologies in the art. Examples of gene targeting technologies include the Cre/Lox system (described in Kühn, R., & M. Torres, R., *Transgenesis Techniques: Principles and Protocols*, (2002), 175-204.), homologous recombination (described in Capecchi, Mario R. *Science* (1989), 244: 1288-1292), TALENs (described in Sommer et al., *Chromosome Research* (2015), 23: 43-55, and Cermak et al., *Nucleic Acids Research* (2011): gkr218.), and CRISPR Cas system as described in Ran FA et al., *Nature Protocols* (2013).

In one embodiment, Type I glutamine synthetase (glnA) inactivation is achieved by a CRISPR/Cas system. CRISPR-Cas and similar gene targeting systems are well known in the art with reagents and protocols readily available (Mali, P. et al., (2013), *Science*, 339(6121), 823-826; Hsu, P. D. et al., (2014), *Cell*, 157.6: 1262-1278.; Jiang et al., *Nature Biotechnology* 31, 233-239 (2013)). Exemplary genome editing protocols are described in Jennifer Doudna, and Prashant Mali, "*CRISPR-Cas: A Laboratory Manual*" (2016) (*CSHL Press*, ISBN: 978-1-621821-30-4) and Ran, F. Ann, et al. *Nature Protocols* (2013), 8 (11): 2281-2308.

A CRISPR endonuclease comprises two components: (1) an RNA-dependent nuclease, typically microbial Cas9; and (2) a short "guide RNA" (gRNA or sgRNA) comprising a ~20 nucleotide targeting sequence that directs the nuclease to a location of interest in the genome. When co-expressed with an artificial sgRNA targeting a cellular gene, the Cas9 endonuclease generates double-stranded breaks of DNA at the targeted locus. This method typically produces small insertions and deletions (indels) that shift the open reading frame (ORF) of the targeted gene and result in premature termination of translation and loss-of-function phenotypes.

In one embodiment, inactivation of the Type I glutamine synthetase (glnA) gene is achieved by site-directed mutagenesis described in *Molecular Cloning*, 3rd Ed., *Current Protocols in Molecular Biology*, and U.S. patent application Ser. No. 12/442,143

In some embodiments, inactivation of the Type I glutamine synthetase (glnA) gene is achieved by deleting the Type I glutamine synthetase (glnA) gene using deletion vectors described in the art (e.g. Argyros et al., 2011. *Appl Environ Microb*. 77, 8288-8294 and in Olson et al. (Olson and Lynd, 2012. *Methods in Enzymology*. 510, 317-30))

In one aspect, the present invention is directed to isolated nucleic acid molecules encoding a mutant Type I glutamine synthetase and capable of conferring enhanced alcohol production from cellulosic substrates to a microorganism.

In some embodiments, the nucleic acid molecule contains one or more nucleotide changes relative to the wild type (native) nucleic acid molecule, which result in a substitution, insertion or deletion of one or more amino acids in the catalytic domain of the protein.

In specific embodiments, the one or more nucleotide changes result in an alteration of one or more amino acids that constitute the active site of the catalytic domain.

In other specific embodiments, the isolated nucleic acid molecule encodes a mutant Type I glutamine synthetase, wherein the mutant protein differs from the wild type protein by a substitution or deletion of a residue that is highly conserved among bacterial species.

In some embodiments, the isolated nucleic acid molecule encodes a mutant Type I glutamine synthetase wherein the mutant protein differs from the wild type protein by a deletion of sequences coding for at least 10, 20, 30, 40, 50, 60, 70, 80, 90, 100, 200, 300 or 400 amino acids.

Biofuels

The genetically engineered microbial strains of the present invention are particularly useful for production of biofuels based on fermentation of biomass materials. Therefore, in a further aspect, the present invention provides a method of producing biofuels from cellulosic biomass based on use of the microbial strains of the present invention that are able to grow at elevated concentrations of ethanol.

Biofuels contemplated by the present invention include particular the types of biologically produced fuels, such as bioalcohols, based on the action of microorganisms and enzymes through fermentation of biomass materials. Examples of bioalcohols include ethanol, butanol, isobutanol, and propanol.

In a typical cellulosic biomass to alcohol process, raw cellulosic biomass material is pretreated in order to convert, or partially convert, cellulosic and hemicellulosic components into enzymatically hydrolyzable components (e.g., poly- and oligo-saccharides). The pretreatment process also serves to separate the cellulosic and hemicellulosic components from solid lignin components also present in the raw cellulosic material. The pretreatment process typically involves reacting the raw cellulosic biomass material, often as a finely divided mixture or slurry in water, with an acid, such as sulfuric acid. Other common pretreatment processes include, for example, hot water treatment, wet oxidation, steam explosion, elevated temperature (e.g., boiling), alkali treatment and/or ammonia fiber explosion. The pretreated biomass is then treated by a saccharification step in which poly- and oligo-saccharides are enzymatically hydrolyzed into simple sugars. The free sugars and/or oligosaccharides produced in the saccharification step are then subjected to fermentation conditions for the production of ethanol or butanol, for example. Fermentation can be accomplished by combining one or more fermenting microorganisms with the produced sugars under conditions suitable for fermentation.

One can also add enzyme to the fermentor to aid in the degradation of substrates or to enhance alcohol production. For example, cellulase can be added to degrade cellulose to glucose simultaneously with the fermentation of glucose to ethanol by microorganisms in the same fermentor. Similarly, a hemicellulase can be added to degrade hemicellulose.

In some embodiments fermentation is carried out as a process called "Consolidated BioProcessing" (CBP). CBP comprises processing cellulose hydrolysis and fermentation simultaneously without the addition of pre-manufactured cellulases. For CBP, the microorganism used for fermentation can be naturally producing cellulases and hemicellulases or the microorganism used for fermentation can be genetically engineered to produce cellulases and hemicellulases. *Clostridium thermocellum* is a suitable thermophilic CBP host because of its high cellulose decomposition rate.

For purpose of fermentation, one strain or a mixture of several strains, some or all of which display enhanced tolerance to ethanol or other inhibitors, can be used.

Specific fermentation conditions can be determined by those skilled in the art, and may depend on the particular feedstock or substrates, the microorganisms chosen and the type of biofuel desired.

After fermentation, alcohol is separated from the fermentation broth by any of the many conventional techniques known to separate alcohol from aqueous solutions, including evaporation, distillation, solvent extraction and membrane separation. Particles of substrate or microorganisms may be removed before separation to enhance separation efficiency.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Example 1

Materials and Methods

Plasmid and Strain Construction

All enzymes and reagents used for cloning were purchased from NEB (Ipswich, Mass.), unless otherwise specified. *Escherichia coli* Top10 (dam$^+$ dcm$^+$; Invitrogen, Carlsbad, Calif.) and BL21 (dam$^+$ dcm$^-$; New England Biolabs, Ipswitch, Mass.), used for plasmid construction and propagation, respectively, were grown aerobically on LB medium supplemented with 12 µg/ml chloramphenicol as required for plasmid maintenance. Plasmid isolation and purification was performed using QIAprep spin miniprep kits (QIAGEN, Germantown, Md.). Plasmid pNJ22::2031_del for deletion of glnA (Clo1313_2031) was constructed using Gibson Assembly according to the manufacture's using primers listed Tables 1-3.

TABLE 1

Primers for pNJ22::2031_del construction via Gibson assembly

| Primer Name | Sequence |
|---|---|
| Gib_2031_up_fwd | ATTTTGTTTCCCATAGGCGCGCCGATATTTTTAAATACTCAATCAAAACAC ATTTTGCTCTG (SEQ ID NO: 1) |
| Gib_2031_up_NotI_rev | CACGCATAATTAGCCGAGAATATGGCCAGCGGCCGCTAAGATTTTCTAAGA TAAGTCGGTGGTT (SEQ ID NO: 2) |
| Gib_2031_down_fwd | TGGCCATATTCTCGGCTAATTATGCG (SEQ ID NO: 3) |
| Gib_2031_down_rev | TTCAATAGTTTAGATAAAAATAATTAATTTTTTAAACGGAACAATTTATA TTCACGGAAACAGTGG (SEQ ID NO: 4) |

TABLE 1-continued

Primers for pNJ22::2031_del construction via Gibson assembly

| Primer Name | Sequence |
|---|---|
| Gib_2031_Cat2_Hpt2_fwd | TTAAAAAATTAATTATTTTTTATCTAAACTATTGAA (SEQ ID NO: 5) |
| Gib_2031_Cat2_Hpt2_rev | ATGAATACATTTCAGGTTTCAAAACGCC (SEQ ID NO: 6) |
| Gib_2031_int_fwd | GGCGTTTTGAAACCTGAAATGTATTCATAATCCCCTTTGTCAAGGGCGCCATATC (SEQ ID NO: 7) |
| Gib_2031_int_rev | TATACACTCCGCTAGCGCGGATCCGATAGGATGAGTTATAATATAAAAATAAAAGAGGTGCTG (SEQ ID NO: 8) |

TABLE 2 pNJ22::2031_del sequencing primers

| Primer Name | Sequence |
|---|---|
| 2031_del_S1 | CCCTCTAGGCGCATAGGAAC (SEQ ID NO: 9) |
| 2031_del_S2 | CCATAACGATTTCGTTGTAAGAAG (SEQ ID NO: 10) |
| 2031_del_S3 | ATGAATACCCGTTCTGTATC (SEQ ID NO: 11) |
| 2031_del_S4 | CAATAGCGACGGAGAGTTAGG (SEQ ID NO: 12) |
| 2031_del_S5 | TTGATTACAGAAGAAGAGTTGAAGG (SEQ ID NO: 13) |
| 2031_del_S6 | TCATAATCCCCTTTGTCAAGG (SEQ ID NO: 14) |

TABLE 3

Primers for Clo1313_2031 deletion verification

| Primer Name | Sequence |
|---|---|
| 2031_Int_F | TTTAAGAATATTTCTTGAATCTCCCTC (SEQ ID NO: 15) |
| 2031_Int_R | TATAAAAATAAAAGAGGTGCTGGAGTT (SEQ ID NO: 16) |
| 2031_Int2_F | GCCTAAAATGTTTCTTACAAAACTACT (SEQ ID NO: 17) |
| 2031_Int2_R | GACTTCATATTAATATATCTCTTTCAAAGG (SEQ ID NO: 18) |
| 2031_Flank_F | TTGACCATTTTTCAATTTATTATTCATC (SEQ ID NO: 19) |
| 2031_Flank_R | AAAATTGTCTGGGACAAAGATATATTG (SEQ ID NO: 20) |

TABLE 4

Expected band sizes (bp) in the parent strain, merodiploid, and deletion strain

| Wild Type | Merodiploid | Deletion |
|---|---|---|
| 331 | 331 | 0 |
| 485 | 0 | 0 |
| 2668 | 3727 | 1339 |

Figure 4:
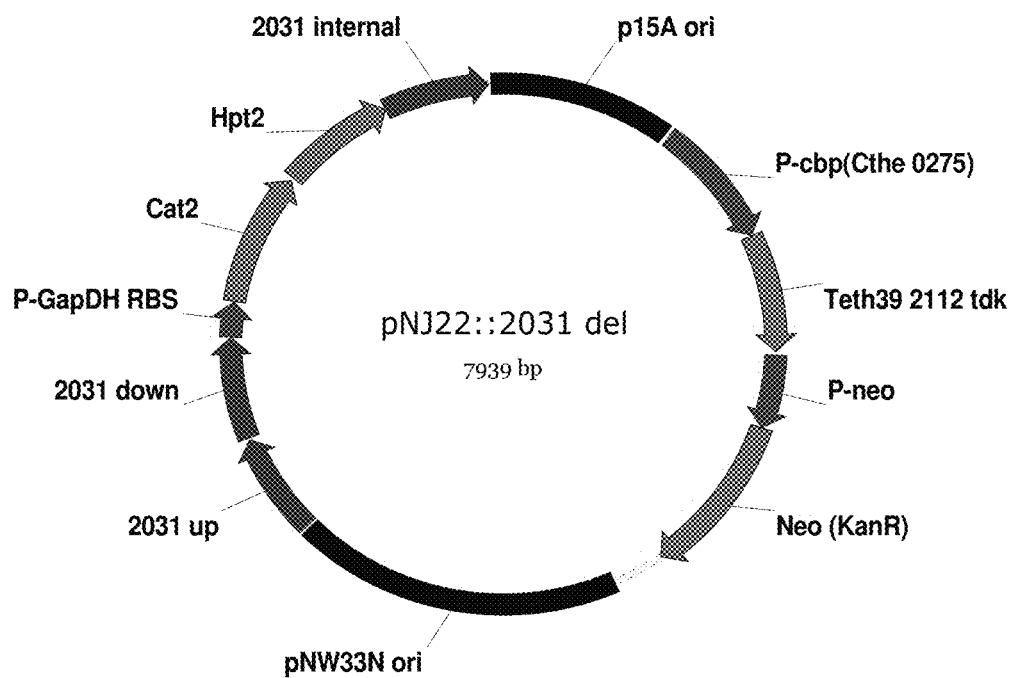
FIG. 4. Key elements of pNJ22::2031_del used for deletion of Type I glutamine synthetases encoded by Clo1313_2031 (glnA). p15A ori, *E. coli* origin of replication; P-cbp, *C. thermocellum* cellobiose phosphorylase promoter; Teth39 2112 tdk, *Thermoanaerobacter pseudethanolicus* thymidine kinase; P-neo, neomycin phosphotransferase promoter; Neo (KanR), neomycin phosphotransferase conferring kanamycin resistance; pNW33N ori, *C. thermocellum* origin of replication; 2031 up, upstream sequence of homology to Clo1313_2031; 2031 down, downstream sequence of homology to Clo1313_2031; P-GapDH RBS, *C. thermocellum* glyceraldehyde-3-phosphate dehydrogenase promoter and ribosome binding site; Cat2, chloramphenicol acetyltransferase; Hpt2, hypoxanthine phosphoribosyltransferase; 2031 internal, internal sequence of homology to Clo1313_2031.

Briefly, Phusion polymerase amplified, DpnI digested PCR fragments corresponding to regions 500 bp upstream, downstream, and within the first 500 bp of Clo1313_2031 coding region, and a 1388 bp fragment encoding a chloramphenicol acetyltransferase (cat) and a hypoxanthine phosphoribosyltransferase (hpt) driven by a *C. thermocellum* glyceraldehyde-3-phosphate (GapDH) promoter, were ligated with EcoRV digested pNJ022 using Gibson assembly generating pNJ22::2031_del (FIG. 4). Correct assembly of fragments was verified using restriction digests and sequencing using primers provided in Tables 1-3. All plasmids used for *C. thermocellum* transformations were ultimately isolated from *E. coli* dam$^+$ dcm$^-$ BL21 (Guss, A. M. et al., 2012. *Biotechnology for Biofuels*. 5, 30).

Figure 5:
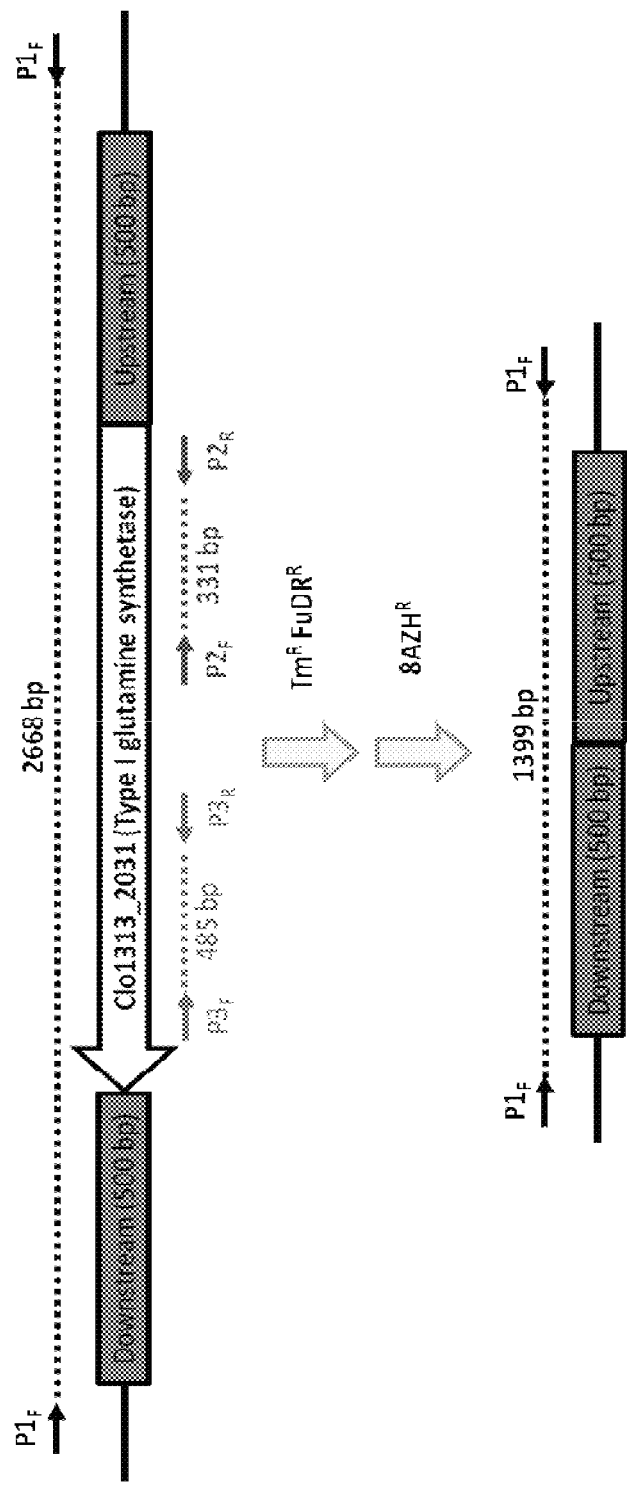
FIG. 5. Deletion of Clo1313_2031 (glnA); overview and confirmation. Clo1313_2031 was deleted according to the protocol outlined by Argyrose et al. (2011). Primer binding sites used to amplify the locus encompassing Clo1313_2031 (P1) and internal to Clo1313_2031 (P2 and P3) and corresponding expected product sizes in the parent and mutant strain are indicated. B) PCR confirmation of Clo1313_2031 deletion. Primer set P1 amplified the chromosomal region that includes Clo1313_2031, and results in a 2668 bp fragment in the parent strain and a 1399 bp fragment in Clo1313_2031 deletion strain. Primer sets P2 and P3 amplified 331 bp and 485 bp fragments of the Clo1313_2031 gene, respectively, in the Δhpt strain, but not in ΔglnA. Reduction in size of the P3 amplicon and absence of P1 and P2 amplicons confirms deletion of Clo1313_2031 in the mutant strain.

*Clostridium thermocellum* DSM 1313 (Deutsche Sammlung von Microorganismen and Zellkulturen, Braunschwieg, Germany) derivatized strains were routinely grown anaerobically at 55° C., unless otherwise specified, in a Coy anaerobic chamber (Coy Laboratory Products, Grass Lake, Mich.) on 5 g/l cellobiose in CTFUD medium (Rydzak et al., 2015. *J Ind Microbiol Biot.* 42, 1263-1272). Medium was made anaerobic via autoclaving to remove $O_2$ from solution, followed by immediate transfer to the anaerobic chamber to maintain anaerobicity. Medium was supplemented with 10 μg/ml thiamphenicol, 50 μg/ml 5-fluoro-2'-deoxyuridine, or 500 μg/ml 8-azahypoxanthine (Tokyo Chemical Industry, Co., Tokyo, Japan) during *C. thermocellum* strain construction when appropriate. All selection steps were performed at 50° C. *C. thermocellum* Δhpt (Argyros et al., 2011. *Appl Environ Microb.* 77, 8288-8294) was transformed via electroporation as previously described (Guss et al., 2012. *Biotechnology for Biofuels*. 5, 30; Olson and Lynd, 2012. *Methods in Enzymology.* 510, 317-30). The glnA gene was deleted according to the protocol developed in Argyros et al. (Argyros et al., 2011. *Appl Environ Microb.* 77, 8288-8294) and detailed in Olson et al. (Olson and Lynd, 2012. *Methods in Enzymology.* 510, 317-30) using plasmid pNJ22::2031_del. Gene deletion was confirmed using primer sets provided in Tables 1-3 as shown in FIG. 5. Deletion of glnA was further confirmed via whole genome resequencing and RNA-seq analysis (discussed below). Culture purity was routinely confirmed via 16S sequencing.

Fermentation Conditions

Fermentation experiments were performed at 55° C. in sealed, nitrogen sparged Balch tubes (27 ml; Belco Glass Inc., Vineland, N.J.) containing 10 ml of MTCS medium supplemented with 4.5 g/l cellobiose as previously described (Rydzak et al., 2015. *J Ind Microbiol Biot.* 42, 1263-1272). Tubes were inoculated with 2% exponential phase ($OD_{600}$ ~0.4) cultures grown on MTCS. Final fermentation product, amino acid, biomass, and pH measurements were taken following complete cellobiose utilization (<0.25 mM remaining). Fermentations were performed a minimum of three times with three independent biological replicates each time. Samples for RNA-seq and metabolomic analysis were grown at 55° C. in sealed, nitrogen sparged 162 ml serum bottles containing 50 ml of MTCS supplemented with 4.5 g/l cellobiose. Samples were harvested in early exponential phase ($OD_{600}$ ~0.33) and analysis was performed in quadruplicate for each strain. To monitor growth rates, cells were grown in 48 well microtitre plates (Corning, Tewksbury, Mass.) containing 600 µl MTCS in an Eon Microplate Spectrophotometer (BioTek Instruments Inc., Winooski, Vt.) situated in a Coy anaerobic chamber. All chemicals were reagent grade and obtained from Sigma-Aldrich (St. Loius, Mo.) or Fisher Scientific (Waltham, Mass.) unless otherwise specified.

Analytical Measurements

Cell growth was monitored spectrophotometrically at $OD_{600}$ in an Eon Microplate Spectrophotometer (BioTek Instruments Inc., Winooski, Vt.). Cellobiose, glucose, and fermentation products (pyruvate, lactate, acetate, formate, ethanol) were analyzed using a Breeze High Performance Liquid Chromatography system (Waters, Milford, Mass.) using an Aminex-HPX-87H column (Bio-Rad, Hercules, Calif.) with a 5 mM sulfuric acid mobile phase. $H_2$ was measured using an Agilent Technologies 6850 Series II Gas Chromatograph (Agilent Technologies, Santa Clara, Calif.) using a thermoconductivity detector set at 190° C. with a $N_2$ reference flow and a Carbonex 1010 PLOT (30.0 m×530 µm I.D.; model Supelco 25467) column. Secreted amino acids were measured using an Aracus Amino Acid Analyzer (membraPure, Berlin, Germany) using a T111 Li-cation exchange column with eluents supplied by the manufacturer. Ninhydrin derived amino acids were measured photometrically at 570 nm with the exception of proline, which was measured at 440 nm. Final pH was measured using an Accument AB15 Basic pH meter (Fisher Scientific; Pittsburg, Pa.). Total nitrogen and carbon in cell pellets was were determined using a Simadzu TOC-Vcph Total Organic Carbon analyzer with added Total Nitrogen unit and a ASI-V autosampler (Shimadzu Scientific Instruments, Columbia, Md.) with an Avicel and glycine standard for carbon and nitrogen determination, respectively (Holwerda et al., 2012. *J Ind Microbiol Biot.* 39, 943-947).

Whole Genome Resequencing

Genome resequencing and analysis was performed by the DOE Joint Genome Institute (JGI, Walnut Creek, Calif.) with an Illumina MiSeq instrument. Genomic DNA was extracted using a Qiagen DNeasy kit (Qiagen, Valencia, Calif.). 100 ng of DNA was sheared to 500 bp fragments using the Covaris LE220 ultrasonicator (Covaris) and size selected using AMPure XP SPRI beads (Beckman Coulter). The fragments were treated with end-repair, A-tailing, and ligation of Illumina compatible adapters (IDT, Inc) using the KAPA-Illumina library creation kit (KAPA Biosystems). The prepared libraries were quantified using KAPA Biosystem's next-generation sequencing library qPCR kit and run on a Roche LightCycler 480 real-time PCR instrument. The quantified libraries were then multiplexed in a pool of 10 and sequenced on the Illumina MiSeq sequencer using a MiSeq Reagent kit, v2, following a 2×150 indexed run recipe.

Paired-end reads were aligned to the reference genome (NC_017992) using Burrows-Wheeler transform (Li and Durbin, 2009. *Bioinformatics.* 25, 1754-1760) and putative SNPs and small indels were called using samtools and mpileup (Li et al., 2009. *Bioinformatics.* 25, 2078-9). Putative structural variants were called using a combination of BreakDancer (filtered to quality 90+) (Chen et al., 2009. *Nat Methods.* 6, 677-81), and Pindel (Ye et al., 2009. *Bioinformatics.* 25, 2865-71). Variants occurring in less than 90% of the reads and variants that were identical to those of the parent Δhpt strain (i.e., due to errors in the reference sequence) were filtered out. Raw data is available from the JGI Sequence Read Archive (JGI Project Id: 1064732).

RNA Isolation and Ribosomal RNA Removal

Pelleted cells, 50 mL from each sample, were resuspended in 1 mL of TRIzol (Invitrogen, Carlsbad, Calif., USA) and lysed by bead beating with 0.8 g of 0.1 mm glass beads (BioSpec Products, Bartlesville, Okla., USA) for 3×20 seconds each at 6,500 rpm in a Precellys 24 high-throughput tissue homogenizer (Bertin Technologies, Montigny-le-Bretonneux, France). The RNA from each cell lysate was purified, DNaseI-treated, and quantity and quality assessed, as previously described (Yang et al., 2012. *BMC Genomics.* 13, 336). High quality total RNA (RIN>8) was depleted of rRNA using Ribo-Zero rRNA Removal Kit for bacteria (Epicentre-Illumina, San Diego, USA) following the manufactures protocol. The depleted sample was purified on a RNA Clean & Concentrator-5 (Zymo Research, Irvine, Calif., USA) following the manufacturer's protocol.

Library Preparation and Sequencing

Depleted RNA was used for RNA-Seq library preparation with the Epicentre ScriptSeq v2 RNA-Seq Library Preparation Kit (Epicentre-Illumina, San Diego, Calif., USA) following the to the manufacturer's protocol (EPILIT329 Rev.C). Agencount AMPure beads (Beckman Coulter, Indianapolis, USA) were used to purify the cDNA, and unique indexes were added during 13 cycles of library amplification. The final RNA-Seq libraries were purified with Agencount AMPure beads (Beckman Coulter, Indianapolis) and quantified with a Qubit fluorometer (Life Technologies, Carlsbad, Calif., USA). The library quality was assessed on a Bioanalyzer DNA 7500 DNA Chip (Agilent, Santa Clara, Calif., USA), and samples were pooled and diluted. Sequencing was completed using a SR50 sequencing protocol on an Illumina HiSeq 2500 platform (HudsonAlpha Genomic Services Laboratory; Huntsville, Ala.).

RNA-Seq Analysis

Raw reads were mapped to genome [GenBank: CP002416] using CLC Genomics Workbench version 8.0 (CLC bio, Aarhus, Denmark) and the default settings for prokaryote genomes. Counts of uniquely mapped reads were analyzed for differential gene expression by DESeq2. Filtering was applied to identify those genes with an FDR <0.05 and a greater than a $log_2$ of +/−1 for differential gene expression. Raw RNA-Seq data have been deposited in NCBI Sequence Read Archive under accession SRP070709 and gene expression data under NCBI GEO accession GSE78219.

Metabolite Extraction and Sample Preparation for Quantification

Metabolites were extracted from *Clostridium thermocellum* cultures in a Coy anaerobic chamber (Grass Lake, Mich.) to maintain anaerobic conditions throughout the extraction procedure. Ten milliliters of culture (removed with a 10 ml syringe) was deposited by vacuum filtration onto a 0.2 um nylon membrane (47 mm diameter). The membrane was then placed (cells down) into 1.5 ml cold (−20° C. or on dry ice) extraction solvent (20:20:10 v/v/v acetonitrile, methanol, water) in a small petri disk and swirled. After a few moments the filter was inverted (cells up) and a pipette used to pass the solvent over the surface of the membrane several times to maximize extraction. Finally, the cell extract was centrifuged at 14,000 RPMs for 5 min to remove cell debris and the supernatant was and stored at −80° C. To measure extracellular metabolites, 2 ml of media was collected by filtration using a 0.22 um syringe filter and stored at −80.

Cell extracts from *E. coli* (K-12 substrain MG1655 rph$^+$ ilvG$^+$) grown in 13C-glucose were used as internal standards for quantitation of metabolites in *C. thermocellum* strains. *E. coli* cells were grown aerobically to an OD$_{600}$ of ~0.45 in M9 minimal medium containing 0.4% universally labeled 13C-glucose as sole carbon source. To assure complete labeling of metabolites in *E. coli*, inoculation was performed using 1/50 dilution from an overnight culture that was also grown on 13C-labeled glucose. *E. coli* metabolites were extracted in a similar manner to the procedure used for *C. thermocellum* (above), but under aerobic (benchtop) conditions.

*C. thermocellum* extracts were mixed with 13C-labeled *E. coli* extracts in ratios of 1:5, 1:1, 5:1 and 1:0 (no 13C labeled internal standards). These mixed samples were then fully dried under a stream of nitrogen and subsequently re-suspended with solvent A (below) in half the initial volume. Samples were then centrifuged to remove particulates, transferred to HPLC vials, and analyzed by HPLC/MS.

2.9 Metabolite Quantification

Samples were analyzed using an HPLC-MS/MS system consisting of a Dionex UHPLC coupled by electrospray ionization (ESI; negative mode) to a hybrid quadrupole—high-resolution mass spectrometer (Q Exactive orbitrap, Thermo Scientific) operated in full scan mode for detection of targeted compounds based on their accurate masses and retention times (matched to purified standards). Liquid chromatography (LC) separation was achieved using an ACQUITY UPLC® BEH C18 (2.1×100 mm column, 1.7 μm particle size). Solvent A was 97:3 water:methanol with 10 mM tributylamine (TBA) and approximately 9.8 mM acetic acid, pH ~8.2; solvent B was 100% methanol. Total run time was 24.5 min with the following gradient: 0 minutes, 5% B; 2.5 minutes, ramp from 5% B to 95% B over 14.5 minutes; hold at 95% B for 2.5 minutes; return to 5% B over 0.5 minutes; hold at 5% B for 5 minutes. All samples were injected twice (analytical replicates). MS scans consisted of full MS scanning for m/z between 70-1000 from time 0 to 18.5 minutes. Exceptions were: m/z of 207-210 excluded between 2-3 min.; and m/z 190-192 excluded between 11-12 minutes. Metabolite peaks were identified using Metabolomics Analysis and Visualization Engine (MAVEN) (Clasquin et al., 2012. John Wiley & Sons, Inc., pp. 14.11.1-14.11.23; Melamud et al., 2010. *Anal Chem*. 82, 9818-9826).

Calculations

CO$_2$ produced was calculated based on the expected equimolar ratio of C1:C2 compounds plus the additional CO$_2$ liberated via valine biosynthesis, whereby CO2=[(ethanol+acetate)−(formate)]+valine. Ratios of oxidized to reduced fermentation products (O/R) were calculated using reduction values of each fermentation product, calculated as the number of oxygen atoms less one-half the number of hydrogens in each compound (Moat et al., 2002). Carbon bound electron equivalents were calculated as described by Harris et al. (Harris and Adams, 1979. *Appl Environ Microbiol*. 37, 237-43) and were used to determine electron recovery.

Example 2

Genomic Analysis of Nitrogen Assimilation

Figure 6:
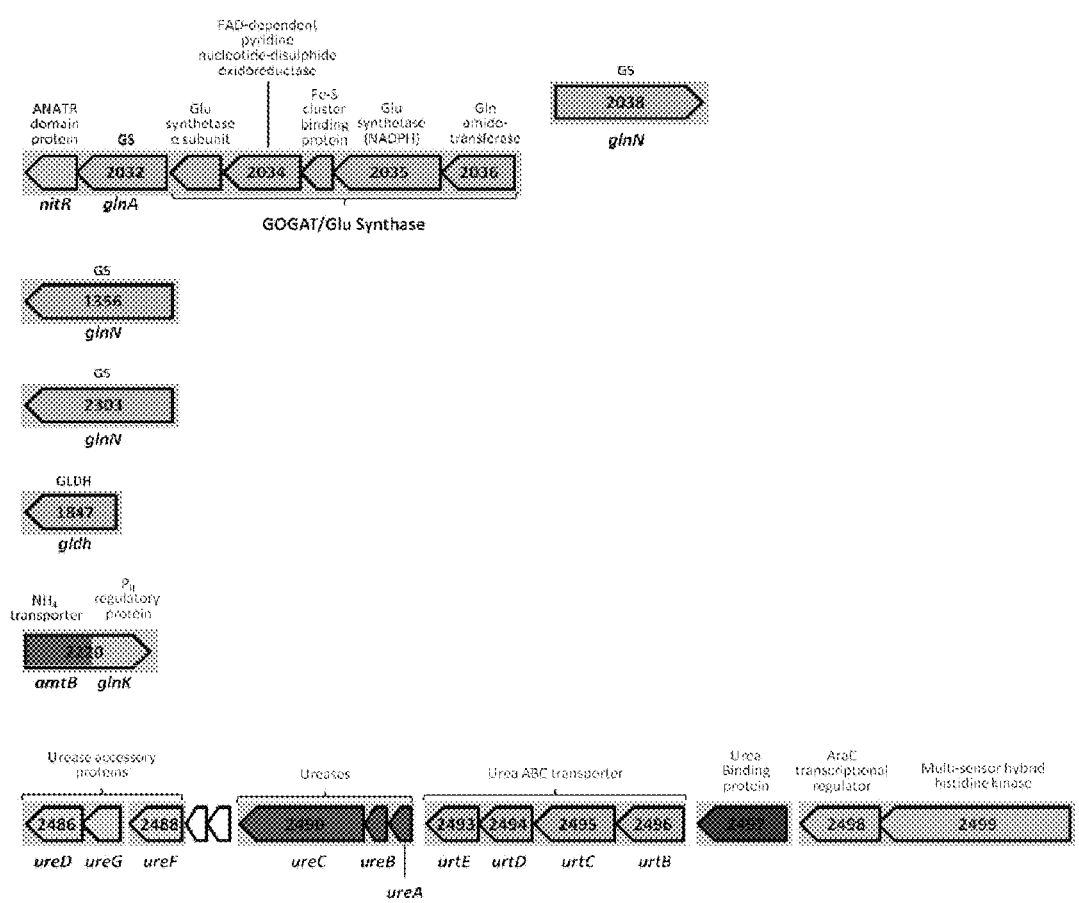
FIG. 6. Organization of genes and predicted operons involved in nitrogen assimilation (green), ammonium transport (blue), urea metabolism (purple), and putative regulation (orange). Predicted operons are highlighted in grey.

The genome of *C. thermocellum* encodes one NADPH-dependent glutamate dehydrogenase (gldh; Clo1313_1847), one cluster of glutamine-oxoglutarate aminotransferase/glutamate synthase type enzymes (gogat; Clo1313_2032-2036), and four glutamine synthetases, including three Type III glutamine synthetases (glnN; Clo1313_1357, 2038, 2303), and one Type I glutamine synthetase (glnA; Clo1313_2031) (FIG. 1). Biocyc (Karp, 2005. *Abstr Pap Am Chein S*. 229, U1178-U1178; Romero and Karp, 2004, *Bioinformatics*. 20, 709-U342) and DOOR (Dam et al., 2007; Mao et al., 2009) predict Clo1313_2030-2036 to be a single operon, and the electron carrier is unknown. Organization of genes and predicted operons involved in nitrogen assimilation are provided in FIG. 6. In principle, any two of these three pathways (GLDH, GOGAT, and GS) should be sufficient to assimilate NH$_4$, but the energetic cost differs depending on whether the ATP-hydrolyzing GS is utilized. Clo1313_2030 is predicted to encode an ANTAR domain protein/response regulator receiver (nitR) that is associated with regulation of nitrogen metabolism. Ammonium is likely transported by Clo1313_2260, which is an apparent fusion protein of an ammonium transporter (AmtB) with the regulatory protein GlnK (also called P$_{II}$). Urea is known to be a nitrogen source for *C. thermocellum*, and it encodes a urease gene cluster, including genes encoding the urease enzyme (Clo1313_2490-2492), urease maturation genes (Col1313_2486-2488), and a urea transporter (Clo1313_2493-2497). *C. thermocellum* also encodes putative nitrogenase subunits nifD, nifK, and nifH (Clo1313_2331, 2332, and 2339, respectively); however, nitrogenase activity has not been detected and N$_2$ does not seem to serve as a nitrogen source (Kridelbaugh et al., 2013. *Bioresource Technol*. 130, 125-135.).

Example 3

Figure 2:
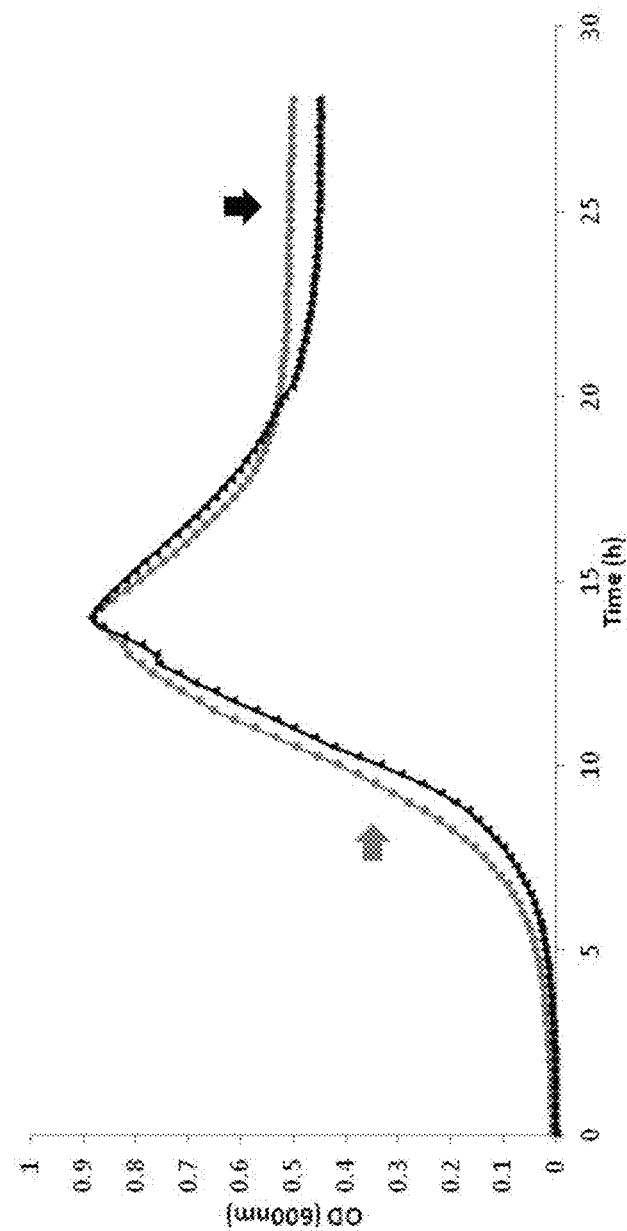
FIG. 2. Growth profiles of parent and mutant strains on defined medium (MTC$_5$). Grey line with circular data points, Δhpt; black line with triangular data points, ΔglnA. Grey and black arrows indicates time of sampling for RNA-seq and end-product analysis, respectively.

Deletion of Type I Glutamine Synthetase Decreases Amino Acid Secretion and Increases Ethanol Production The glnA gene, Clo1313_2031, encoding the sole Type I glutamine synthetase was deleted in *C. thermocellum* Δhpt, hereafter referred to as ΔglnA. The parent strain *C. thermocellum* Δhpt and ΔglnA were grown on 4.5 g/l (13.1 mM) cellobiose in defined medium (MTC$_5$). Deletion of glnA had no impact on growth, as both Δhpt and ΔglnA strains grew to a final OD$_{600}$ of ~0.88 and had a mid-exponential phase generation time of 1.3 h(±0.1) (FIG. 2). Total elemental carbon in cell pellets for Δhpt and ΔglnA was 0.252(±0.010) and 0.269 g/l(±0.017), respectively (corresponding to 21.0 and 22.4 mM of carbon, respectively), and total pellet nitrogen was 0.062(±0.001) and 0.069 (0.002) g/l, respectively, further demonstrating that deletion of glnA had no significant impact on microbial biomass production. Interestingly, the initial pH of MTC$_5$ (pH=7.43±0.06) decreased to only 6.64±0.13 in ΔglnA cultures versus 5.86±0.16 in Δhpt cultures.

Figures 3A, 3B:
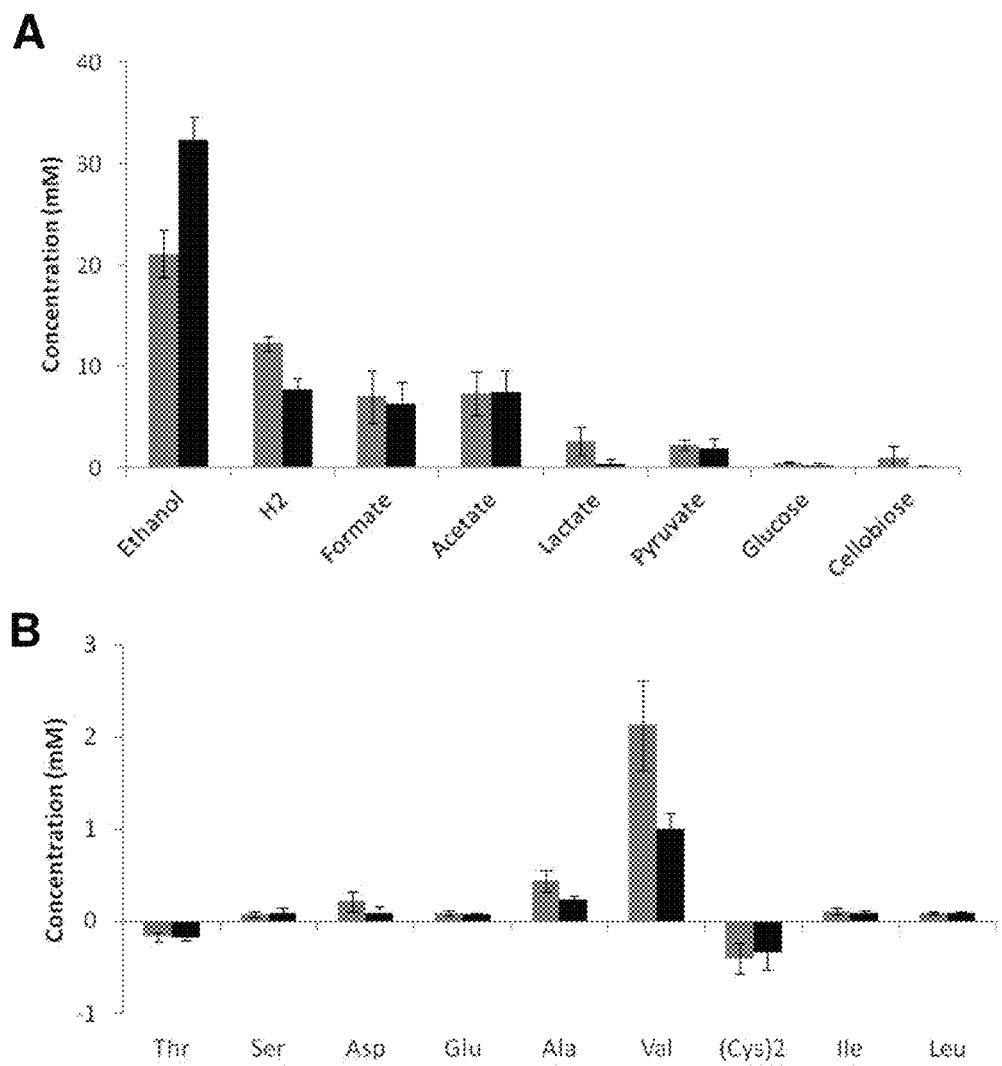
FIG. 3A-3B. Final fermentation products (A) and secreted amino acids (B) of *C. thermocellum* strains. All products were measured upon completion of cellobiose utilization. Grey bars, Δhpt; black bars, ΔglnA; (Cys)2, cystine. Only amino acids with a change of greater than 0.8 mM compared to MTC$_5$ medium are shown.

Fermentation products were measured following near-completion of cellobiose utilization (<1.0 mM remaining), approximately 10 hours after peak OD was reached. Deletion of glnA increased ethanol production by 53%, improving ethanol yields from 0.86 to 1.22 moles per mole hexose equivalent (FIG. 3A, Table 4). While negligible changes in formate, acetate, and extracellular pyruvate were observed, lactate production was nearly completely abolished and H$_2$ production decreased by 38%. Furthermore, total amino acid secretion decreased by 44%, with the most abundant secreted amino acids, valine and alanine, decreasing by 53% and 46%, respectively (FIG. 3B). Conversely, carbon and electron recoveries from canonical fermentation products and biomass increased by 9.5% and 8.6%, respectively, in ΔglnA fermentations (Table 4), demonstrating that additional carbon and electron flux is diverted from secreted amino acids to canonical fermentation products. While total carbon and electron recoveries were both c.a. 100% in ΔglnA fermentations, recoveries were 4.3% and 4.9% lower, respectively, in Δhpt fermentations, suggesting that some products may be unaccounted for in the latter.

Example 4

Unintended Mutations are Unlikely to be Responsible for High-Ethanol Yielding Phenotype During strain construction, unintended mutations can be fixed in the population due to the single colony purification steps. While most of these mutations do not result in a noticeable phenotype, it was possible that unintended mutations were responsible for increased ethanol production in ΔglnA. Therefore, the mutant strain was resequenced and compared to the parent strain. A total of 7 high-confidence mutations were found in ΔglnA (Table 5). As expected, resequencing analysis identified the deletion of glnA. Three genes in ΔglnA had non-synonymous mutations. These included genes encoding (i) a family 18 glycoside hydrolase predicted by KOG and CAZy to be a chitinase, (ii) a protein of unknown function UPF0017, and (iii) a hemerythrin-like metal-binding protein found upstream of chemotaxis protein CheC. One 35 bp deletion was identified upstream and within the coding region of a putative methyl-accepting chemotaxis sensory transducer, eliminating the ribosome binding site and ATG start codon. Two other mutations were found in intergenic regions (Table 2) that could have altered expression of the adjacent genes. RNAseq analysis (see below) revealed that only expression of the hypothetical protein Clo1313_1767 was affected (increased 4-fold).

To rule out the possibility that these mutations are the cause of the high-ethanol yielding phenotype observed in ΔglnA, we reconstructed the deletion again from the parent strain. We again observed a 42% increase in ethanol production compared to the Δhpt, elimination of lactate production, and a decrease in $H_2$ production, further solidifying that deletion of glnA is responsible for the substantial increase in ethanol production.

Example 5

Expression of Genes Involved in Nitrogen Metabolism Increased in ΔglnA

To elucidate the mechanism of increased ethanol production and decreased amino acid secretion in ΔglnA, we performed RNA-seq analysis of ΔglnA and the parent strain on mid-exponential phase batch cultures ($OD_{600}$ ~0.35). 3009 and 3031 genes were identified with a minimum average of two reads per gene for Δhpt and ΔglnA, respectively. Of these genes, 151 were shown to be differentially expressed by a factor >2 and a p-value <0.05.

While Type I glutamine synthetase was the most highly expressed glutamine synthetase (Rank 532; 5264 average reads) in Δhpt, Clo1313_1357 encoding one of the three Type III glutamine synthetases was also highly expressed (Rank 634; 4410 average reads). The two other Type III glutamine synthetases (Clo1313_2038 and Clo1313_2303) were expressed at low levels (1256 and 25 average reads, respectively) in Δhpt. However, in ΔglnA, expression of Clo1313_2038 and Clo1313_2303 increased by 13 and 77-fold, respectively. The putative pseudogene Clo1313_2037, annotated as an aspartate ammonia ligase and located upstream of Clo1313_2038, was also upregulated 9.7-fold. While Clo1313_2030-2036 are predicted to be an operon by DOOR and Biocyc, three of these subunits (Clo1313_2034-2036) increased by 19-40-fold in ΔglnA, while subunits Clo1313_2032-2033 and Clo1313_2030 increased only 1.7- to 1.9-fold. Notably, Clo1313_2034-2036 were expressed at much lower levels (~17-449 average reads) when compared to those of the other genes in the predicted operon (2623-7082 average reads) in Δhpt. No significant change in expression was observed for glutamate dehydrogenase (Clo1313_1847).

Deletion of glnA also caused a strong increase in expression of genes involved in urea uptake and metabolism. The Clo1313_2486-2499 gene cluster, encoding a multi-sensor hybrid histidine kinase and a two component AraC family transcriptional regulator (Clo1313_2499 and Clo1313_2498, respectively), a urea binding protein (Clo1313_2497), the urea ABC transporter (Clo1313_2493-2496), and urease (Clo1313_2490-2492) and urease accessory protein (Clo1313_2486-2488), were upregulated 6.7 to 81-fold in ΔglnA. Additionally, the ammonium transporter-$P_{II}$ fusion (Clo1313_2260) was also upregulated by 35-fold in the deletion strain.

Two additional gene clusters were also upregulated. First, genes encoding an RNF-complex (Clo1313_0061-0066) involved in electron transfer reactions between ferredoxin and NADH were upregulated 1.6 to 2.9-fold. Similarly, a gene cluster (Clo1313_0073-0080) encoding a putative glycerol kinase (Clo1313_0073), transketolase (Clo1313_0074-0075), alcohol dehydrogenase GroES domain protein (Clo1313_0076), ABC transporter (Clo1313_0077-0079), and phosphoglycerate mutase (Clo1313_0080) was also upregulated 2.4 to 3.4-fold. An increase was also observed in the transcription of some genes involved in protein synthesis, sporulation/germination, and a proton-translocating pyrophosphatase.

While a number of genes were down-regulated, the decrease was less pronounced than the increase in gene clusters encoding genes involved in urea metabolism and nitrogen assimilation, Expression of the most highly down-regulated gene (Clol1313_2176), encoding a 4626 amino acid protein with an S-layer homology domain (SLH), decreased 4.3-fold in ΔglnA. Other down-regulated genes include putative copper amine oxidases, genes predicted to be involved in carbohydrate hydrolysis, putative fatty acid metabolism genes, and Type II excretion system proteins predicted to be involved in pilus assembly.

Example 6

Intracellular Glutamine Levels are Higher in ΔglnA

Metabolomic analysis was performed to evaluate changes in metabolite pools in ΔglnA. A total of 53 metabolites were identified, including nine in which extracellular concentrations prevented accurate quantification of intracellular levels. In these cases, changes in extracellular levels are used as a proxy for intracellular changes. Fourteen metabolites had significant changes relative to the parent strain. Notably, glutamine levels increased 6.4-fold and extracellular α-ketoglutarate levels increased 5.5-fold in ΔglnA, while glutamate levels remained the same. Threonine and dihydroxyoorotate levels increased 7.2 and 4.9-fold, respectively. While $NADP^+$ levels increased 2.6-fold, NADPH, NAD$^+$, and NADH pools did not change. GDP and GTP levels increase 2.9 and 1.8-fold respectively. Ornithine, the only metabolite measured in the urea cycle, also increased 1.8-fold. Conversely, the only intracellular metabolite with decreased levels in the mutant strain was acetyl-CoA levels, which decreased 2.5-fold.

Metabolic engineering strategies aimed at simultaneously eliminating all canonical organic fermentation products, including lactate, acetate, formate, and decreasing H$_2$ through elimination of an [FeFe] hydrogenase maturation factor, have improved C. thermocellum ethanol yields to ~70% of theoretical (Papanek et al., 2015. Metab Eng. 32, 49-54). However, additional strategies are needed to redirect flux away from non-traditional fermentation products such as amino acids. To further optimize ethanol yields, carbon and electron flux must be redirected away from away from secreted amino acid towards ethanol. Deletion of Type I glutamine synthetase not only reduced secreted amino acids by 44%, but also improved ethanol production by 53%. Remarkably, disruption of this nitrogen assimilation gene had a more significant improvement on ethanol yields than independent deletions of ldh (Argyros et al., 2011. Appl Environ Microb. 77, 8288-8294; Biswas et al., 2014. PloS one. 9, e86389), pta (Tripathi et al., 2010. Appl Environ Microb. 76, 6591-9) or pfl (Rydzak et al., 2015. J Ind Microbiol Biot. 42, 1263-1272).

Deletion of the lone Type I glutamine synthetase (glnA) induced deregulation of nitrogen metabolism. Despite the presence of excess ammonium (28 mM) and urea (33.3 mM) in the medium, genes encoding urea metabolism and transport, ammonium transport, and ammonium assimilation, including GOGAT and two alternative Type III glutamine synthetases, were highly upregulated. The upregulation of urea metabolism genes increased the rate of urea breakdown to ammonia (and CO$_2$), resulting in a higher final pH of ΔglnA when compared to Δhpt cultures. Furthermore, the upregulation of GOGAT is responsible for the observed increase of intracellular glutamine and α-ketoglutarate levels in ΔglnA. Given that glutamate levels are comparable in both ΔglnA and the parent strain, while glutamine and alpha-ketoglutarate levels are higher in ΔglnA, glutamate must be aminated to glutamine via GOGAT or glutamine synthetase, While deletion of the Type I glutamine synthetase was compensated by an increase in expression of two of the three encoded Type III glutamine synthetases, previous reports have shown that glutamine synthetase activity can be feedback inhibited by glutamine (Deuel and Prusiner, 1974. J. Biol Chem, :249, 257-264). Therefore, flux may be limited through glutamine synthetases in ΔglnA due to elevated intracellular glutamine levels. Furthermore, the increase in both glutamine and α-ketoglutarate levels were comparable in the ΔglnA strain, suggesting that the majority of flux towards glutamine occurs via GOGAT. Thus, the decrease in secreted amino acid seems counterintuitive. However, most transamination reactions involved in amino acid synthesis use glutamate as the amino donor, rather than glutamine (Reitzer, 2003. Annu Rev Microbiol. 57, 155-176), producing α-ketoglutarate. Because α-ketoglutarate levels were 5-fold higher while intracellular glutamate levels did not change in ΔglnA, the thermodynamics of transamination would be less favorable, possibly resulting in decreased rates of amino acid production. Furthermore, the decrease in NADPH to NADP$^+$ ratios in ΔglnA also decreases the free energy of NADPH-dependent anabolic amino acid reactions.

Similar changes in expression of genes involved in nitrogen metabolism have been observed in response to ethanol stress in C. thermocellum ATCC 27405 (Yang et al., 2012. BMC Genomics. 13, 336). Specifically, genes encoding urea transport and metabolism, two Type III glutamine synthetases (Clo1313_2038, 2303), and the first 3 subunits of GOGAT (Clo1313_2034-2036) were up-regulated in response to ethanol stress. However, Type I glutamine synthetase and ammonium transporter-P$_{II}$ fusion were not differentially expressed. Given that ethanol production increased in ΔglnA, it is possible that increased ethanol concentrations may have contributed to the changes in expression of nitrogen metabolism genes, but the concentration of added ethanol in the previous study was substantially higher than the amount produced here. Treatment of C. thermocellum chemostat cultures with methyl viologen, which also improved ethanol yields, resulted in a decrease in expression of genes encoding one of the three Type III glutamine synthetases (Clo1313_2303) and the first 3 subunits of GOGAT (Clo1313_2034-2036) (Sander et al., 2015. Biotechnol Biofuels. 8, 211), demonstrating that up-regulation of nitrogen assimilation genes does not always directly correlate with increasing ethanol concentrations.

A number of effector molecules, including ammonium, glutamine, and α-ketoglutarate, have been shown to regulate nitrogen metabolism through gene expression and/or protein activity. While ammonium is the active nitrogen effector in Actinobacteria such as Corynebacterium glutamicum (Muller et al., 2006. Journal of Biotechnology. 126, 440-453; Nolden et al., 2001. Mol Microbiol. 42, 1281-1295; Rehm and Burkovski, 2011. Appl Microbiol Riot. 89, 239-248; Rehm et al., 2010, Microbiol-Sgm. 156, 3180-3193), glutamine and α-ketoglutarate are the primary effectors in Proteobacteria bacteria (Ikeda et al., 1996. J Mol Biol. 259, 589-607; Jiang et al., 1998. Biochemistry. 37, 12802-10; Reitzer, 2003. Annu Rep Microbiol. 57, 155-176) and Firmicutes such as Bacillus subtilis (Wray et al., 2001. Cell. 107, 427-35). In the latter organisms, high ratios of glutamine to α-ketoglutarate are typically indicative of nitrogen-rich conditions. In enteric bacteria, glutamine acts as a metabolic signal for nitrogen availability, whereby the two-component Ntr regulatory system activates transcription of nitrogen metabolism genes in response to decreased intracellular glutamine levels during nitrogen-limited growth (Magasanik, 1996. Escherichia coli and Salmonella: Cellular and Molecular Biology. ASM Press, Washington, D.C., pp. 1344-1356; Zimmer et al., 2000. Proc Natl Acad Sci USA. 97, 14674-9). In B. subtilis, glutamine can inhibit activity of glutamine synthetase (Deuel and Prusiner, 1974. J Biol Chem. 249, 257-264). Furthermore, this feedback-inhibited form of glutamine synthetase can directly interact with the global transcriptional regulator TnrA, preventing it from both binding DNA and activating expression of genes involved in ammonium transport, urea metabolism, and ammonium assimilation under nitrogen rich conditions (Wray et al., 2001. Cell. 107, 427-35). Conversely, TnrA-regulated genes were constitutively expressed in B. subtilis glnA mutants (Wray et al., 1996, Proc Natl Acad Sci. USA. 93, 8841-5). While no TnrA homologue was identified in C. thermocellum, it is feasible that an alternative MerR-family protein may act as a transcriptional regulator of nitrogen metabolism genes and respond to feedback-inhibited glutamine synthetase. In C. thermocellum, it would be logical to assume that a 6.4-fold increase in intracellular glutamine levels, as observed in ΔglnA, would lead to decreased expression of nitrogen metabolism genes. However, given that nitrogen metabolism genes were overexpressed in ΔglnA, despite the increase in intracellular glutamine levels, it may be possible that *C. thermocellum* GlnA has an analogous regulatory role to that of the *B. subtilis* GlnA.

Perhaps the most surprising consequence of deletion of glnA was the 53% increase in ethanol production. While redirecting carbon and electron flux away from secreted amino acids towards canonical fermentation products could, in part, explain increased ethanol yields, the increase in ethanol production (approximately 10 mM) far exceeds the decrease in amino acid secretion (approximately 1 mM), suggesting additional mechanisms for improved ethanol yields. The increase in ethanol can potentially be explained by increased NADH availability for ethanol production due to a combination of increased flux through Rnf and GOGAT. In *C. thermocellum*, catabolism of pyruvate to acetyl-CoA via pyruvate:ferredoxin oxidoreductase (PFOR) generates reduced ferredoxin (Rydzak et al., 2014. *Microbiol Biotechnol.* 98, 6497-510; Rydzak et al., 2009. *Journal of Biotechnology.* 140, 169-75; Rydzak et al., 2012. *BMC Microbiology.* 12, 214), which is not a direct electron donor for ethanol production. This reduced ferredoxin is typically reoxidzed through either $H_2$ formation via Ech or bifurcating hydrogenase, NADPH formation via NADH-dependent reduced ferredoxin:$NADP^+$ oxidoreductase (NfnAB) (Rydzak et al., 2014. *Appl. Microbial Biotechnol.* 98, 6497-510; Wang et al., 2010. Journal of Bacteriology. 192, 5115-23), or NADH formation using Rnf. Given the decrease in $H_2$ production, decrease in NADPH:$NADP^+$ ratios, and increase in Rnf expression in ΔglnA, it is likely that. Rnf is transferring electrons from ferredoxin to produce NADH, which in turn can be directly used to reduce acetyl-CoA into ethanol. While steady state ratios of NADH:$NAD^+$ did not change in ΔglnA, levels of intracellular acetyl-CoA decreased 2.5-fold, suggesting that increased rates of NADH production may accelerate acetyl-CoA reduction into ethanol.

While previous genetic engineering strategies were successful in improving ethanol yields in *C. thermocellum* though elimination of canonical fermentation pathways, ethanol yields still were still too low, in part due to amino acid secretion. Deletion of the Type I glutamine synthetase (glnA) not only reduced amino acid secretion, but also increased ethanol production by 50%, demonstrating that genetic manipulation of nitrogen assimilation pathways is a promising strategy for improving product yields in *C. thermocellum* and potentially other organisms. Deletion of glnA increased expression of nitrogen assimilation, ammonium transport, and urea uptake and metabolism, despite the presence of excess nitrogen. These changes are typically indicative of a nitrogen starvation response, but excess nitrogen was present during growth, and that glutamine and α-ketoglutarate levels increased, suggesting that nitrogen metabolism was deregulated in response to deletion of glnA.

TABLE 4

Final product yields and fermentation balances of Δhpt and ΔGlnA on 4.5 g/l cellobiose in batch cultures grown in $MTC_5$. Carbon recoveries of fermentation products including biomass carbon (FPs), secreted amino acids (AAs), and total secreted products are provided.

| | Product Yields (mol mol-hexose consumed$^{-1}$) | | | | | | Biomass | | C recovery (%)[3] | | | e- recovery (%)[3] | | |
|---|---|---|---|---|---|---|---|---|---|---|---|---|---|---|
| CTFUD | Ethanol | $H_2$ | Formate | Acetate | Lactate | $CO_2$[1] | carbon | O/R balance[2] | FPs | AAs | Total | FPs | AAs | Total |
| Δhpt | 0.86 | 0.50 | 0.29 | 0.30 | 0.11 | 0.96 | 0.85 | 1.03 | 85.8 | 8.9 | 94.6 | 86.0 | 10.3 | 96.4 |
| ΔglnA | 1.22 | 0.29 | 0.24 | 0.28 | 0.01 | 1.31 | 0.85 | 1.07 | 96.3 | 4.6 | 99.9 | 95.3 | 5.4 | 100.1 |

[1]$CO_2$ was calculated using C1:C2 ratio using ethanol, acetate and formate concentrations.
[2]O/R balance was determined using formate, calculated $CO_2$ (from C1:C2 ratio), $H_2$ and ethanol.
[3]Carbon and electron recoveries were calculated based on all substances (cellobiose and glucose) and end-products (ethanol, $H_2$, formate, acetate, lactate, pyruvate,) detected, calculated $CO_2$ (from $C_1:C_2$ ratio), secreted amino acids, and elemental carbon biomass measurements

TABLE 5

High confidence mutations found in ΔglnA that are not found in the parent Δhpt strain.
INS, insertion; DEL, deletion. Changes in amino acids within coding region mutations are indicated

| Position | | | | | | |
|---|---|---|---|---|---|---|
| Start | Stop | Strand | Region | Locus tags | Genes | Type |
| 2395922 | 2397259 | − | CODING | Clo1313__2031 | glutamine synthetase, type I (glnA) | DEL |
| 491357 | 491357 | + | CODING | Clo1313__0436 | glycoside hydrolase family 18 | W258R |
| 2327020 | 2327020 | − | CODING | Clo1313__1979 | protein of unknown function UPF0027 | D360E |
| 3494201 | 3494201 | + | CODING | Clo1313__2980 | hemerythrin-like metal-binding protein | V45E |
| 2131552 | 2131586 | − | CODING/ INTERGENIC | Clo1313__1820 Clo1313__1476 (up) | methyl-accepting chemotaxis sensory transducer Peptidase S7 flavivirus helicase (NS3) | DEL INS |
| 1728952 | 1728952 | + | INTERGENIC | Clo1313__1477 (down) Clo1313__1767 (up) | glycoside hydrolase family 9 Hypothetical protein | INS |
| 2060557 | 2060557 | − | INTERGENIC | Clo1313__1768 (down) | cellulosome anchoring protein cohesin region | |

What is claimed is:

1. A genetically engineered bacteria strain with enhanced alcohol production from cellulosic substrates, wherein said bacteria strain comprises an inactivated Type I glutamine synthetase (glnA) gene.

2. The bacteria strain of claim 1, wherein said bacteria strain is a strain of *Clostridium*.

3. The bacteria strain of claim 1, wherein said bacteria strain is a strain of *Clostridium thermocellum* (*C. thermocellum*).

4. The bacteria strain of claim 1, wherein the inactivation of the Type I glutamine synthetase (glnA) gene in said bacteria strain is achieved by a method selected from the group consisting of CRISPR/Cas system, Cre/Lox system, TALEN system, and homologous recombination.

5. The bacteria strain of claim 1, wherein said bacteria strain further comprises at least one inactivated gene selected from the list consisting of spoOA encoding a master regulator of sporulation, NfnAB complex encoding the ferredoxin-NADH:NADP+ oxidoreductase, ppdK encoding pyruvate:phosphate dikinase, mdh encoding malate dehydrogenase, mae encoding malic enzyme, pta encoding phosphotransacetylase, pfl encoding pyruvate:formate lyase, ldh encoding lactate dehydrogenase, hydG encoding [FeFe] hydrogenase maturation factor, and ech endocing [NiFe] Ech-type hydrogenase.

6. The bacteria strain of claim 1, wherein said bacteria strain further comprises at least one overexpressed gene selected from the list consisting of Rnf encoding Ferredoxin:NADH oxidoreductase, PDC encoding pyruvate decarboxylase, adhE encoding bifunctional aldehyde/alcohol dehydrogenase, and pryK encoding pyruvate kinase.

7. A method of producing alcohol from a cellulosic substrate, comprising adding cells of the genetically modified bacteria strain of claim 1 to a fermentation mixture, allowing said cells to ferment and produce alcohol, and recovering the alcohol produced.

8. The method of claim 7, wherein the produced alcohol is ethanol.

9. The method of claim 7, wherein the produced alcohol is butanol.

10. The method of claim 7, wherein the produced alcohol is isobutanol.

11. The method of claim 7, wherein fermentation is carried out at a temperature of about 50-65° C.

12. The method of claim 7, wherein the efficiency of alcohol production is at least 70% of a theoretical maximum of 2 moles alcohol per mole hexose.

13. The method of claim 7, wherein said bacteria strain is a strain of *Clostridium*.

14. The method of claim 7, wherein said bacteria strain is a strain of *Clostridium thermocellum* (*C. thermocellum*).

15. The method of claim 7, wherein said bacteria strain further comprises at least one inactivated gene selected from the list consisting of spoOA encoding a master regulator of sporulation, NfnAB complex encoding the ferredoxin-NADH:NADP+ oxidoreductase, ppdK encoding pyruvate:phosphate dikinase, mdh encoding malate dehydrogenase, mae encoding malic enzyme, pta encoding phosphotransacetylase, pfl encoding pyruvate:formate lyase, ldh encoding lactate dehydrogenase, hydG encoding [FeFe] hydrogenase maturation factor, and ech endocing [NiFe] Ech-type hydrogenase.

16. The method of claim 7, wherein said bacteria strain further comprises at least one overexpressed gene selected from the list consisting of Rnf encoding Ferredoxin:NADH oxidoreductase, PDC encoding pyruvate decarboxylase, adhE encoding bifunctional aldehyde/alcohol dehydrogenase, and pryK encoding pyruvate kinase.

17. A method of enhancing alcohol production of a bacteria strain from cellulosic substrates, comprising inactivating in said bacteria strain the endogenous gene coding for Type I glutamine synthetase (glnA).

18. The method of claim 17, wherein the inactivation of the Type I glutamine synthetase (glnA) gene in the bacteria is achieved by a method selected from the group consisting of CRISPR/Cas system, Cre/Lox system, TALEN system, and homologous recombination.

* * * * *